United States Patent
Busch et al.

(10) Patent No.: US 6,906,189 B2
(45) Date of Patent: Jun. 14, 2005

(54) CATALYSTS AND METHODS FOR CATALYTIC OXIDATION

(75) Inventors: Daryle Hadley Busch, Lawrence, KS (US); Simon Robert Collinson, Nottingham (GB); Timothy Jay Hubin, McPherson, KS (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/228,854

(22) Filed: Aug. 27, 2002

(65) Prior Publication Data

US 2003/0036473 A1 Feb. 20, 2003

Related U.S. Application Data

(63) Continuation of application No. 10/155,105, filed on May 24, 2002, now abandoned, which is a continuation of application No. 09/380,672, filed as application No. PCT/IB98/000302 on Mar. 6, 1998, now abandoned.
(60) Provisional application No. 60/040,629, filed on Mar. 7, 1997, now abandoned.

(51) Int. Cl.$^7$ ..................... C07D 225/00; C07D 223/10
(52) U.S. Cl. .......................... 540/465; 540/486; 546/2; 510/376
(58) Field of Search ................... 540/465, 486; 510/376; 546/2

(56) References Cited

U.S. PATENT DOCUMENTS

| | | | | |
|---|---|---|---|---|
| 4,156,683 A | * | 5/1979 | Lehn | 260/338 |
| 4,257,955 A | * | 3/1981 | Gansow et al. | 260/338 |
| 4,497,737 A | * | 2/1985 | Sargeson et al. | 260/239 BC |
| 4,888,032 A | | 12/1989 | Busch | |
| 5,126,464 A | * | 6/1992 | Burrows et al. | 549/520 |
| 5,153,161 A | | 10/1992 | Kerschner et al. | |
| 5,162,508 A | * | 11/1992 | Lehn et al. | 534/15 |
| 5,272,056 A | | 12/1993 | Burrows et al. | |
| 5,329,024 A | | 7/1994 | Jureller et al. | |
| 5,356,554 A | | 10/1994 | Delwel et al. | |
| 5,374,416 A | * | 12/1994 | Rousseaux et al. | 424/2 |
| 5,409,627 A | | 4/1995 | Boskamp | |
| 5,409,633 A | | 4/1995 | Clements et al. | |
| 5,417,959 A | * | 5/1995 | Wallace | 424/9.363 |
| 5,428,180 A | | 6/1995 | Burrows et al. | |
| 5,429,769 A | | 7/1995 | Nicholson et al. | |
| 5,433,884 A | | 7/1995 | Altieri et al. | |
| 5,434,069 A | | 7/1995 | Tsaur et al. | |
| 5,441,660 A | | 8/1995 | Tsaur et al. | |
| 5,457,185 A | * | 10/1995 | Lehn et al. | 534/15 |
| 5,460,743 A | | 10/1995 | Delwel et al. | |
| 5,466,390 A | | 11/1995 | Houghton et al. | |
| 5,480,575 A | | 1/1996 | Altieri et al. | |
| 5,480,577 A | | 1/1996 | Nicholson et al. | |
| 5,480,990 A | | 1/1996 | Kiefer et al. | |
| 5,484,555 A | | 1/1996 | Schepers | |
| 5,504,075 A | | 4/1996 | Burrows et al. | |
| 5,550,301 A | | 8/1996 | Bhinde et al. | |
| 5,977,353 A | * | 11/1999 | Argese et al. | 540/473 |
| 5,980,864 A | * | 11/1999 | Platzek et al. | 424/9.363 |
| 6,042,810 A | * | 3/2000 | Ripa et al. | 424/9.363 |
| 6,218,351 B1 | | 4/2001 | Busch et al. | |
| 6,225,464 B1 | | 5/2001 | Hiler, II et al. | |
| 6,306,812 B1 | | 10/2001 | Perkins et al. | |
| 6,342,597 B1 | * | 1/2002 | Geremia et al. | 540/465 |
| 6,387,862 B2 | * | 5/2002 | Busch et al. | 510/511 |
| 6,399,557 B2 | | 6/2002 | Perkins et al. | |
| 6,417,354 B1 | * | 7/2002 | Geremia et al. | 540/465 |
| 6,444,808 B2 | | 9/2002 | Hiler, II et al. | |
| 6,566,318 B2 | * | 5/2003 | Perkins et al. | 510/310 |
| 6,608,015 B2 | * | 8/2003 | Busch et al. | 510/311 |
| 2001/0044401 A1 | * | 11/2001 | Perkins et al. | 510/367 |
| 2002/0193271 A1 | * | 12/2002 | LaBeque | 510/311 |

FOREIGN PATENT DOCUMENTS

| | | |
|---|---|---|
| EP | 0 458 39 8 A2 | 11/1991 |
| WO | WO 94/03271 A1 | 2/1994 |
| WO | WO 95/10217 | 4/1995 |
| WO | WO 95/19185 | 7/1995 |
| WO | WO 95/19347 | 7/1995 |
| WO | WO 95/20353 | 8/1995 |
| WO | WO 95/30733 | 11/1995 |
| WO | WO 95/34628 | 12/1995 |
| WO | WO 98/39406 | 9/1998 |

OTHER PUBLICATIONS

Chemical Abstract, vol. 125, No. 4, Jul. 22, 1996, XP002068240.
Chemical Abstract, vol. 113, No. 25, Dec. 17, 1990, XP00268241.
J.S. Bradshaw et al., "Heterocyclic Compounds: Aza–crown Macrocycles", 1993, Wiley–Interscience.
Hudson et al., Chemical Reviews, 1993, pp. 861–885.
G.R. Weisman et al., J. Amer. Chem. Soc., 1990, 112, p. 8604.
B.K. Coltrain et al., "Oxygen Activation by Transition Metal Complexes of Macrobibyclic Cyclident Ligands", "The Activation of Dioxygen and Homogeneous Catalytic Oxidation", 1993, Plenum Press, NY, pp. 359–380.

(Continued)

*Primary Examiner*—David Sample
*Assistant Examiner*—J. Pasterczyk
(74) *Attorney, Agent, or Firm*—James F. McBride; Kim W. Zerby; Steve W. Miller

(57) ABSTRACT

Catalytic systems and methods for oxidizing materials in the presence of metal catalysts (preferably manganese-containing catalysts) complexed with selected macropolycyclic rigid ligands, preferably cross-bridged macropolycyclic ligands. Included are using these metal catalysts in such processes as: synthetic organic oxidation reactions such as oxidation of organic functional groups, hydrocarbons, and heteroatoms, including enantiomeric epoxidation of alkenes, enynes, sulfides to sulfones and the like; oxidation of oxidizable compounds (e.g., stains) on surfaces such as fabrics, dishes, countertops, dentures and the like; oxidation of oxidizable compounds in solution, dye transfer inhibition in the laundering of fabrics; and further in the bleaching of pulp and paper products.

4 Claims, No Drawings

OTHER PUBLICATIONS

Hancock et al., "J. Chem. Coc. Chem. Commun.," 1987, pp. 1129–1130.

Weisman et al., "Synthesis and Transition Metal Complexes of New Cross–Bridget Tetraamine Ligands", Chem. Commun., 1996, pp. 947–948.

Weisman et al., J. Amer. Chem. Soc., 1990, 112(23), pp. 8604–8605.

Ramasubbu & Wainwright J. Chem. Soc. Chem. Commun., 1982, pp. 277–278.

Kojimia et al., Chemistry Letters, 1996, pp. 153–154.

Wainwright, Inor. Chem, 1980, 19(5), pp. 1396–1398.

Mali, Wade & Hancock, J. Chem Soc., Dalton Trans., 1992, 1, pp. 67–71.

Mol. Crys. Liq. Cryst. Sci. Technol., Sect. A, 1996, 276, pp. 79–84.

Mol. Crys. Liq. Cryst. Sci. Technol., Sect. A, 1996, 276, pp. 85–90.

Mol. Crys. Liq. Cryst. Sci. Technol., Sect. A, 1996, 278, pp. 235–240.

Koek et al., J. Chem. Soc. Dalton Trans., 1996, pp. 353–362.

Wieghardt et al., Angew Chem. Internat. Ed. Engl., 1986(m) 25, pp. 1030–1031.

Wieghardt et al., J. Amer. Chem. Soc., 1988, 110, p. 7398.

Ciampolini et al., J. Chem. Soc., Dalton Trans., 1984, pp. 1357–1362.

Hancock et al., Inorg. Chem., 1990, 29, pp. 1968–1974.

Izatt et al., Chem. Rev., 1995, 95, pp. 2529–2586.

Bryan et al., Inorganic Chemistry, 1975, 14, No. 2., pp. 296–299.

Costa & Delgado, Inorg. Chem., 1993, 32, pp. 5257–5265.

Hancock et al., Inorganica Chimica Acta., 1989, 164, pp. 73–84.

Bencini et al., J. Chem. Soc. Chem. Comm., 1990, pp. 174–175.

Hancock & Martell, Chem. Rev., 1989, 89, pp. 1875–1914.

D.H. Busch, Chemical Reviews, 1993, 93, pp. 847–860.

Zimmer, Chemical Reviews, 1995, 95(38), pp. 2629–2648.

H.T. Witteveen et al., J. Inorg. Nucl. Chem., 1974, 36, p. 1535.

Chem. Commun. Issue 8, 1996, cover page Apr. 21, 1996.

* cited by examiner

CATALYSTS AND METHODS FOR CATALYTIC OXIDATION

CROSS-REFERENCE

This application is a continuation and claims priority under 35 U.S.C. § 120 to U.S. application Ser. No. 10/155,105, filed May 24, 2002, (now abandoned) which in turn is a continuation and claims priority to U.S. application Ser. No. 09/380,672, filed Sep. 7, 1999, (now abandoned) which is an entry into the U.S. National Stage under 35 U.S.C. § 371 of PCT International Application Serial No. PCT/IB98/00302, filed Mar. 6, 1998, which claims priority under PCT Article 8 and 35 U.S.C. § 119(e) to U.S. Provisional Application Ser. No. 60/040,629, filed Mar. 7, 1997 (now abandoned).

TECHNICAL FIELD

The present invention relates to catalytic systems and methods for oxidizing materials in the presence of catalysts which are complexes of transition metals such as Mn, Fe or Cr, with selected macropolycyclic rigid ligands, preferably cross-bridged macropolycyclic ligands. More specifically, the present invention relates to catalytic oxidation of oxidizable compounds using said metal catalysts, including synthetic organic oxidation reactions as appropriate to chemical process industry, drug synthesis, and the preparation of specialty chemicals, such as enantiomeric epoxidation of alkenes, oxidation of organic functional groups, hydrocarbons, heteroatoms, or enynes, conversion of sulfides to sulfones, and the like; oxidation of oxidizable compounds (e.g., stains) on surfaces such as fabrics, dishes, countertops, dentures and the like; oxidation of oxidizable compounds in solution; dye transfer inhibition in the laundering of fabrics; the decontamination of soils; and further, to the bleaching of pulp and paper. Preferred catalytic systems include transition-metal complexes of ligands which are polyazamacropolycycles, especially including specific azamacrobicycles, such as cross-bridged derivatives of cyclam.

BACKGROUND OF THE INVENTION

A damaging effect of manganese on fabrics during bleaching has been known since the 19th century. In the 1960's and '70's, efforts were made to include simple Mn(II) salts in detergents, but none saw commercial success. More recently, metal-containing catalysts containing macrocyclic ligands have been described for use in bleaching compositions. Such catalysts include those described as manganese-containing derivatives of small macrocycles, especially 1,4,7-trimethyl-1,4,7-triazacyclononane. These catalysts assertedly catalyze the bleaching action of peroxy compounds against various stains. Several are said to be effective in washing and bleaching of substrates, including in laundry and cleaning applications and in the textile, paper and wood pulp industries. However, such metal-containing bleach catalysts, especially these manganese-containing catalysts, still have shortcomings, for example a tendency to damage textile fabric, relatively high cost, high color, and the ability to locally stain or discolor substrates.

Salts of cationic-metal dry cave complexes have been described in U.S. Pat. No. 4,888,032, to Busch, Dec. 19, 1989 as complexing oxygen reversibly, and are taught as being useful for oxygen scavenging and separating oxygen from air. A wide variety of ligands are taught to be usable, some of which include macrocycle ring structures and bridging groups. See also: D. H. Busch, *Chemical Reviews*, (1993), 93, 847–880, for example the discussion of superstructures on polydentate ligands at pages 856–857, and references cited therein, as well as B. K. Coltrain et al., "Oxygen Activation by Transition Metal Complexes of Macrobicyclic Cyclidene Ligands" in "The Activation of Dioxygen and Homogeneous Catalytic Oxidation", Ed. by E. H. R. Barton, et al. (Plenum Press, NY; 1993), pp. 359–380.

More recently the literature on azamacrocycles has grown at a rapid pace. Among the many references are Hancock et. al., *J. Chem. Soc., Chem. Commun.*, (1987), 1129–1130; Weisman et al., "Synthesis and Transition Metal Complexes of New Cross-Bridged Tetraamine Ligands", *Chem. Commun.*, (1996), 947–948; U.S. Pat. No. 5,428,180, U.S. Pat. No. 5,504,075, and U.S. Pat. No. 5,126,464, all to Burrows et al.; U.S. Pat. No. 5,480,990, to Kiefer et al.; and U.S. Pat. No. 5,374,416, to Rousseaux et al.

Homogeneous transition metal catalysis is a broad realm that has enjoyed intensive activity leading to a number of large scale chemical processes; e.g., the Monsanto acetic acid process, the Dupont adiponitrile process, and others, among which certain famous ones involve oxidations (Wacker Process, Midcentury Process). Further, transition metal oxidation catalysis has been promoted heavily in studies on the biomimicry of the monooxygenase enzymes, especially cytochrome P450. Whereas such studies have emphasized and shown the prowess of the native porphyrin prosthetic group, others have shown that certain oxidative capabilities exist in the same metal ions in the simple solvated condition. This history reveals the possibility that catalytic oxidation may alter almost all families of organic compounds to yield valuable products, but successful applications depend on the activity of the putative catalyst, it survivability under reaction conditions, its selectivity, and the absence of undesirable side reactions or over-reaction.

It has now surprisingly been determined that the use of certain transition-metal catalysts of specific rigid macropolycycles, preferably containing cross-bridging, have exceptional kinetic stability such that the metal ions only dissociate very slowly under conditions which would destroy complexes with ordinary ligands, and further have exceptional thermal stability. Thus, the present invention catalyst systems can provide one or more important benefits. These include improved effectiveness and in some instances even synergy with one or more primary oxidants such as hydrogen peroxide, hydrophilically or hydrophobically activated hydrogen peroxide, preformed peracids, monopersulfate or hypochlorite; the ability to be effective catalysts, some, especially those containing Mn(II), having little to no color and allowing great formulation flexibility for use in consumer products where product aesthetics are very important; and effectiveness on a variety of substrates and reactants, including a variety of soiled or stained fabrics or hard surfaces while minimizing tendency to stain or damage such surfaces.

Therefore, the present invention provides improved catalytic systems containing transition-metal oxidation catalysts, and methods which utilize these catalysts and catalytic systems in the area of chemical syntheses involving organic oxidation reactions, such as oxidation of organic functional groups, hydrocarbons, or heteroatoms, and epoxidation of alkenes; oxidation of oxidizable stains on fabrics and hard surfaces; oxidation of reactants in solutions; pulp and paper bleaching; the oxidation of organic pollutants and for other equivalent highly desirable purposes.

These and other objects are secured herein, as will be seen from the following disclosures.

BACKGROUND ART

Transition metals such as manganese are well-known in oxidation systems. Free $Mn^{+2}$ ions have, for example, been implicated in the oxidation of lignin by white rot mycetes. Manganese and other transition metals in complexed form are familiar in biological systems with a variety of ligands. See, for example, "The Biological Chemistry of the Elements", J. J. R. Fraustro da Silva and R. J. P. Williams, Clarendon Press, Oxford, reprinted 1993. Complexes of ligands such as substituted porphyrins with iron, manganese, chromium or ruthenium are asserted to be useful in catalyzing a variety of oxidative reactions, including oxidation of lignin and industrial pollutants. See, for example, U.S. Pat. No. 5,077,394.

A recent review of nickel-catalyzed oxidations includes the following disclosures: (1) simple tetradentate ligands such as cyclam (a non-cross-bridged, N—H functional tetraazamacrocycle) or salen (a four-donor N,N,O,O ligand) render Ni(II) active for olefin epoxidation; (2) Ni salen complexes can utilize sodium hypochlorite as primary oxidant and show high catalytic turnover in epoxidation reactions; (3) bleach can be used under phase-transfer conditions for manganese porphyrin-catalyzed epoxidations and can be adapted to Ni as well; and (4) reactivity is dramatically influenced by pH with conversion of styrenes into epoxides being quantitative under conditions said to be optimized at pH 9.3.

The catalysis of oxidation reactions by transition metals is more generally useful in synthetic organic chemistry in such varied aspects of the chemical process industry as commodity chemical production and drug manufacture, in addition to the laboratory, and also in consumer product applications such as detergency. Laundry bleaching in general is reviewed in Kirk Othmer's Encyclopedia of Chemical Technology, 3rd and 4th editions under a number of headings including "Bleaching Agents", "Detergents" and "Peroxy Compounds". Laundry applications of bleaching systems include the use of amido-derived bleach activators in laundry detergents as described in U.S. Pat. No. 4,634,551. The use of manganese with various ligands to enhance bleaching is reported in the following United States patents: U.S. Pat. No. 4,430,243; U.S. Pat. No. 4,728,455; U.S. Pat. No. 5,246,621; U.S. Pat. No. 5,244,594; U.S. Pat. No. 5,284,944; U.S. Pat. No. 5,194,416; U.S. Pat. No. 5,246,612; U.S. Pat. No. 5,256,779; U.S. Pat. No. 5,280,117; U.S. Pat. No. 5,274,147; U.S. Pat. No. 5,153,161; U.S. Pat. No. 5,227,084; U.S. Pat. No. 5,114,606; U.S. Pat. No. 5,114,611. See also: EP 549,271 A1; EP 544,490 A1; EP 549,272 A1; and EP 544,440 A2.

U.S. Pat. No. 5,580,485 describes a bleach and oxidation catalyst comprising an iron complex having formula $A[LFeX_n]^zY_q(A)$ or precursors thereof. The most preferred ligand is said to be N,N-bis(pyridin-2-yl-methyl)-bis (pyridin-2-yl)methylamine, $N_4Py$. The Fe-complex catalyst is said to be useful in a bleaching system comprising a peroxy compound or a precursor thereof and suitable for use in the washing and bleaching of substrates including laundry, dishwashing and hard surface cleaning. Alternatively, the Fe-complex catalyst is assertedly also useful in the textile, paper and wood-pulp industries.

The art of the transition metal chemistry of macrocycles is enormous; see, for example "Heterocyclic compounds: Aza-crown macrocycles", J. S. Bradshaw et. al., Wiley-Interscience, 1993 which also describes a number of syntheses of such ligands. See especially the table beginning at p. 604. U.S. Pat. No. 4,888,032 describes salts of cationic metal dry cave complexes.

Cross-bridging, i.e., bridging across nonadjacent nitrogens, of cyclam (1,4,8,11-tetraazacyclotetradecane) is described by Weisman et al, *J. Amer. Chem. Soc.*, (1990), 112(23), 8604–8605. More particularly, Weisman et al., *Chem. Commun.*, (1996), pp. 947–948 describe new cross-bridged tetraamine ligands which are bicyclo[6.6.2], [6.5.2], and [5.5.2] systems, and their complexation to Cu(II) and Ni(II) demonstrating that the ligands coordinate the metals in a cleft. Specific complexes reported include those of the ligands 1.1:

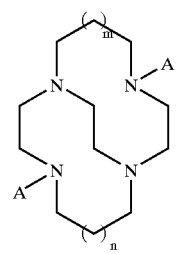

1.1 in which A is hydrogen or benzyl and (a) m=n=1; or (b) m=1 and n=0; or (c) m=n=0, including a Cu(II)chloride complex of the ligand having A=H and m=n=1; Cu(II) perchlorate complexes where A=H and m=n=1 or m=n=0; a Cu(II) chloride complex of the ligand having A=benzyl and m=n= 0; and a Ni(II)bromide complex of the ligand having A=H and m=n=1. In some instances halide in these complexes is a ligand, and in other instances it is present as an anion. This handful of complexes appears to be the total of those known wherein the cross-bridging is not across "adjacent" nitrogens.

Ramasubbu and Wainwright, *J. Chem. Soc., Chem. Commun.*, (1982), 277–278 in contrast describe structurally reinforcing cyclen by bridging adjacent nitrogen donors. Ni(II) forms a pale yellow mononuclear diperchlorate complex having one mole of the ligand in a square planar configuration. Kojima et al, *Chemistry Letters*, (1996), pp. 153–154, describes assertedly novel optically active dinuclear Cu(II) complexes of a structurally reinforced tricyclic macrocycle.

Bridging alkylation of saturated polyaza macrocycles as a means for imparting structural rigidity is described by Wainwright, *Inorg. Chem.*, (1980), 19(5), 1396–8. Mali, Wade and Hancock describe a cobalt (III) complex of a structurally reinforced macrocycle, see *J. Chem. Soc., Dalton Trans.*, (1992), (1), 67–71. Seki et al describe the synthesis and structure of chiral dinuclear copper(II) complexes of an assertedly novel reinforced hexaazamacrocyclic ligand; see *Mol. Cryst. Liq. Cryst. Sci. Technol.*, Sect. A (1996), 276, 79–84; see also related work by the same authors in the same Journal at 276, 85–90 and 278, 235–240. $[Mn(III)_2(\mu-O)(\mu-O_2CMe)_2L_2]^{2+}$ and $[Mn(IV)_2(\mu-O)_3L_2]^{2+}$ complexes derived from a series of N-substituted 1,4,7-triazacyclononanes are described by Koek et al., see *J. Chem. Soc., Dalton Trans.*, (1996), 353–362. Important earlier work by Wieghardt and co-workers on 1,4,7-triazacyclononane transition metal complexes, including those of Manganese, is described in *Angew. Chem. Internat. Ed. Engl.*, (1986), 25, 1030–1031 and *J. Amer. Chem. Soc.*, (1988), 110, 7398.

Ciampolini et al., *J. Chem. Soc., Dalton Trans.*, (1984), 1357–1362 describe synthesis and characterization of the macrocycle 1,7-dimethyl-1,4,7,10-tetraazacyclododecane and of certain of its Cu(II) and Ni(II) complexes including both a square-planar Ni complex and a cis-octahedral complex with the macrocycle co-ordinated in a folded configuration to four sites around the central nickel atom. Hancock et al, *Inorg. Chem.*, (1990), 29, 1968–1974 describe ligand design approaches for complexation in aqueous solution, including chelate ring size as a basis for control of size-based selectivity for metal ions. Thermodynamic data for macrocycle interaction with cations, anions and neutral molecules is reviewed by Izatt et al., *Chem. Rev.*, (1995), 95, 2529–2586 (478 references).

Bryan et al, *Inorg. Chem.*, (1975), 14(2)., 296–299 describe synthesis and characterization of Mn(II) and Mn(III) complexes of meso-5,5,7–12,12,14-hexamethyl-1,4,8,11-tetraazacyclotetradecane ([14]aneN4]. The isolated solids are assertedly frequently contaminated with free ligand or "excess metal salt" and attempts to prepare chloride and bromide derivatives gave solids of variable composition which could not be purified by repeated crystallization.

Costa and Delgado, *Inorg. Chem.*, (1993), 32, 5257–5265, describe metal complexes such as the Co(II), Ni(II) and Cu(II) complexes, of macrocyclic complexes containing pyridine. Derivatives of the cross-bridged cyclens, such as salts of 4,10-dimethyl-1,4,7,10-tetraazabicyclo[5.5.2] tetradecane, are described by Bencini et al., see *Supramolecular Chemistry*, 3., 141–146. U.S. Pat. No. 5,428,180 and related work by Cynthia Burrows and co-workers in U.S. Pat. No. 5,272,056 and U.S. Pat. No. 5,504,075 describe pH dependence of oxidations using cyclam or its derivatives, oxidations of alkenes to epoxides using metal complexes of such derivatives, and pharmaceutical applications. Hancock et al., *Inorganica Chimica Acta.*, (1989), 164, 73–84 describe under a title including "complexes of structurally reinforced tetraaza-macrocyclic ligands of high ligand field strength" the synthesis of complexes of low-spin Ni(II) with three assertedly novel bicyclic macrocycles. The complexes apparently involve nearly coplanar arrangements of the four donor atoms and the metals despite the presence of the bicyclic ligand arrangement. Bencini et al., *J. Chem. Soc., Chem. Commun.*, (1990), 174–175 describe synthesis of a small aza-cage, 4,10-dimethyl-1,4,7,10-15-pentaazabicyclo [5.5.5]heptadecane, which "encapsulates" lithium. Hancock and Martell, *Chem. Rev.*, (1989), 89, 1875–1914 review ligand design for selective complexation of metal ions in aqueous solution. Conformers of cyclam complexes are discussed on page 1894 including a folded conformer—see FIG. 18 (cis-V). The paper includes a glossary. In a paper entitled "Structurally Reinforced Macrocyclic Ligands that Show Greatly Enhanced Selectivity for Metal Ions on the Basis of the Match and Size Between the Metal Ion and the Macrocyclic Cavity", Hancock et al., *J. Chem. Soc., Chem. Commun.*, (1987), 1129–1130 describe formation constants for Cu(II), Ni(II) and other metal complexes of some bridged macrocycles having piperazine-like structure.

Many other macrocycles are described in the art, including types with pedant groups and a wide range of intracyclic and exocyclic substituents. Although the macrocycle and transition metal complex literature are, separately, vast, relatively little appears to have been reported on how to select and combine specific transition metals and specific macrocycle classes, for example cross-bridged tetraaza- and penta-aza macrocycles, so as to apply them for the further improvement of oxidation catalysis. There is, for example, no apparent singling out of these materials from the vast chemical literature, either alone or as their transition metal complexes, for use in bleaching detergents.

SUMMARY OF THE INVENTION

The present invention relates to a method for oxidizing materials, said method comprising contacting (preferably in the presence of a solvent, such as water, non-aqueous solvents, and mixtures thereof) a material capable of being oxidized with an oxidation agent and a transition-metal oxidation catalyst, wherein said transition-metal oxidation catalyst comprises a complex of a transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV), preferably Mn(II), Mn(III), Mn(IV), Fe(II), Fe(III), Fe(IV), Cr(II), Cr(III), Cr(IV), Cr(V), and Cr(VI), preferably Mn, Fe and Cr in the (II) or (III) state, coordinated with a macropolycyclic rigid ligand, preferably a cross-bridged macropolycyclic ligand, having at least 3 donor atoms, at least two of which are bridgehead donor atoms.

The present invention also relates to catalytic systems effective for oxidation of materials comprising: (a) a catalytically effective amount, preferably from about 1 ppb to about 99.9%, more typically from about 0.001 ppm to about 500 ppm, preferably from about 0.05 ppm to about 100 ppm (wherein "ppb" denotes parts per billion by weight and "ppm" denotes parts per million by weight), of a transition-metal oxidation catalyst, wherein said transition-metal oxidation catalyst comprises a complex of a transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV) coordinated with a macropolycyclic rigid ligand, preferably a cross-bridged macropolycyclic ligand, having at least 3 donor atoms, at least two of which are bridgehead donor atoms; and (b) the balance, to 100%, of one or more adjunct materials.

Amounts of the essential transition-metal catalyst and essential adjunct materials can vary widely depending on the precise application. For example, the catalytic systems herein may be provided as a concentrate, in which case the catalyst can be present in a high proportion, for example 0.01%–80%, or more, of the composition. The invention also encompasses catalytic systems at their in-use levels; such systems include those in which the catalyst is dilute, for example at ppb levels. Intermediate level compositions, for example those comprising from about 0.01 ppm to about 500 ppm, more preferably from about 0.05 ppm to about 50 ppm, more preferably still from about 0.1 ppm to about 10 ppm of transition-metal catalyst and the balance to 100%, preferably at least about 0.1%, typically about 99% or more being solid-form or liquid-form adjunct materials (for example fillers, solvents, and adjuncts especially adapted to a particular use (for example papermaking adjuncts, detergent adjuncts, or the like). The invention also encompasses a large number of novel transition-metal catalysts per-se, especially including their substantially pure (100% active) forms.

The present invention preferably relates to catalytic systems effective for oxidation of materials comprising: (a) a catalytically effective amount, preferably from about 1 ppb to about 49%, of a transition-metal oxidation catalyst, said catalyst comprising a complex of a transition metal and a macropolycyclic rigid ligand, preferably a cross-bridged macropolycyclic ligand, wherein:

(1) said transition metal is selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV);

(2) said macropolycyclic rigid ligand is coordinated by at least three, preferably at least four, more preferably four or five, donor atoms to the same transition metal and comprises:

(i) an organic macrocycle ring containing three, preferably four, or more donor atoms (preferably at least 3, more preferably at least 4, of these donor atoms are N) separated from each other by covalent linkages of at least one, preferably 2 or 3, non-donor atoms, two to five (preferably three to four, more preferably four) of these donor atoms being coordinated to the same transition metal in the complex;

(ii) a linking moiety, preferably a cross-bridging chain, which covalently connects at least 2 (preferably non-adjacent) donor atoms of the organic macrocycle ring, said covalently connected (preferably non-adjacent) donor atoms being bridgehead donor atoms which are coordinated to the same transition metal in the complex, and wherein said linking moiety (preferably a cross-bridged chain) comprises from 2 to about 10 atoms (preferably the cross-bridged chain is selected from 2, 3 or 4 non-donor atoms, and 4–6 non-donor atoms with a further donor atom), including for example, a cross-bridge which is the result of a Mannich condensation of ammonia and formaldehyde; and (iii) optionally, one or more non-macropolycyclic ligands, preferably monodentate ligands, such as those selected from the group consisting of $H_2O$, ROH, $NR_3$, RCN, $OH^-$, $OOH^-$, $RS^-$, $RO^-$, $RCOO^-$, $OCN^-$, $SCN^-$, $N_3^-$, $CN^-$, $F^-$, $Cl^-$, $Br^-$, $I^-$, $O_2^-$, $NO_3^-$, $NO_2^-$, $SO_4^{2-}$, $SO_3^{2-}$, $PO_4^{3-}$, organic phosphates, organic phosphonates, organic sulfates, organic sulfonates, and aromatic N donors such as pyridines, pyrazines, pyrazoles, imidazoles, benzimidazoles, pyrimidines, triazoles and thiazoles with R being H, optionally substituted alkyl, optionally substituted aryl (specific examples of monodentate ligands including phenolate, acetate or the like); and (b) at least about 0.1%, preferably B %, of one or more adjunct materials (where B %, the "balance" of the composition expressed as a percentage, is obtained by subtracting the weight of said component (a) from the weight of the total composition and then expressing the result as a percentage by weight of the total composition).

The present invention also preferably relates to catalytic systems effective for oxidation of materials comprising: (a) a catalytically effective amount, as identified supra, of a transition-metal oxidation catalyst, said catalyst comprising a complex of a transition metal and a macropolycyclic rigid ligand (preferably a cross-bridged macropolycyclic ligand) wherein: (1) said transition metal is selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV), and (2) said macropolycyclic rigid ligand is selected from the group consisting of:

(i) the macropolycyclic rigid ligand of formula (I) having denticity of 3 or 4:

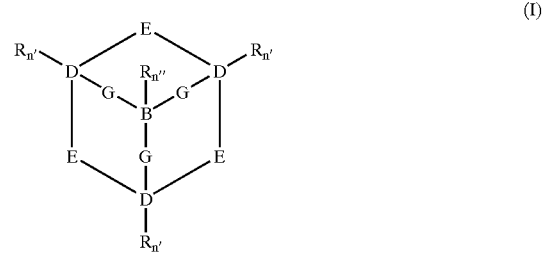

(I)

(ii) the macropolycyclic rigid ligand of formula (II) having denticity of 4 or 5:

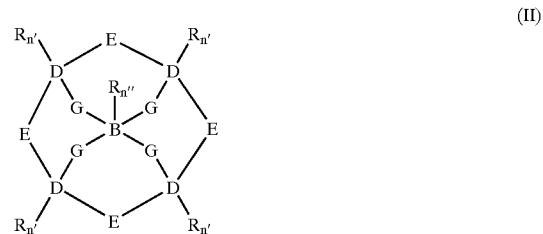

(II)

(iii) the macropolycyclic rigid ligand of formula (IV) having denticity of 5 or 6:

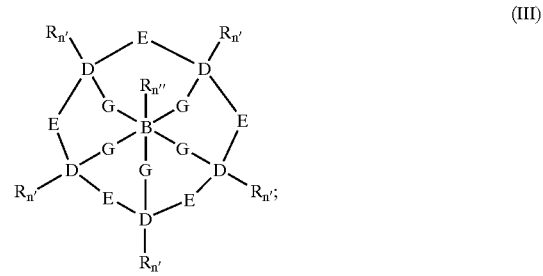

(III)

(iv) the macropolycyclic rigid ligand of formula (IV) having denticity of 6 or 7:

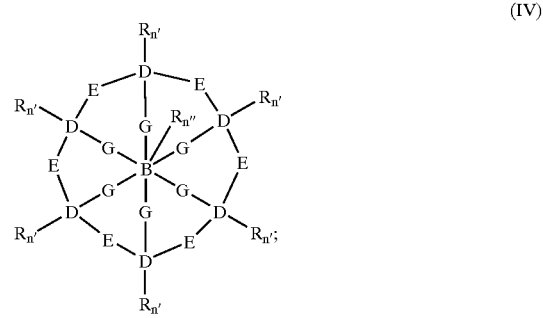

(IV)

wherein in these formulas:

each "E" is the moiety $(CR_n)_a$—X—$(CR_n)_{a'}$, wherein X is selected from the group consisting of O, S, NR and P, or a covalent bond, and preferably X is a covalent bond and for each E the sum of a+a' is independently selected from 1 to 5, more preferably 2 and 3;

each "G" is the moiety $(CR_n)_b$;

each "R" is independently selected from H, alkyl, alkenyl, alkynyl, aryl, alkylaryl (e.g., benzyl), and heteroaryl, or two or more R are covalently bonded to form an aromatic, heteroaromatic, cycloalkyl, or heterocycloalkyl ring;

each "D" is a donor atom independently selected from the group consisting of N, O, S, and P, and at least two D atoms are bridgehead donor atoms coordinated to the transition metal (in the preferred embodiments, all donor atoms designated D are donor atoms which coordinate to the transition metal, in contrast with heteroatoms in the structure which are not in D such as those which may be present in E; the non-D heteroatoms can be non-coordinating and indeed are non-coordinating whenever present in the preferred embodiment);

"B" is a carbon atom or "D" donor atom, or a cycloalkyl or heterocyclic ring;

each "n" is an integer independently selected from 1 and 2, completing the valence of the carbon atoms to which the R moieties are covalently bonded;

each "n'" is an integer independently selected from 0 and 1, completing the valence of the D donor atoms to which the R moieties are covalently bonded;

each "n''" is an integer independently selected from 0, 1, and 2 completing the valence of the B atoms to which the R moieties are covalently bonded;

each "a" and "a'" is an integer independently selected from 0–5, preferably a+a' equals 2 or 3, wherein the sum of all "a" plus "a'" in the ligand of formula (I) is within the range of from about 7 to about 12, the sum of all "a" plus "a'" in the ligand of formula (II) is within the range of from about 6 (preferably 8) to about 12, the sum of all "a" plus "a'" in the ligand of formula (III) is within the range of from about 8 (preferably 10) to about 15, and the sum of all "a" plus "a'" in the ligand of formula (IV) is within the range of from about 10 (preferably 12) to about 18;

each "b" is an integer independently selected from 0–9, preferably 0–5 (wherein when b=0, $(CR_n)_0$ represents a covalent bond), or in any of the above formulas, one or more of the $(CR_n)_b$ moieties covalently bonded from any D to the B atom is absent as long as at least two $(CR_n)_b$ covalently bond two of the D donor atoms to the B atom in the formula, and the sum of all "b" is within the range of from about 1 to about 5; and (iii) optionally, one or more non-macropolycyclic ligands; and (b) adjunct materials at suitable levels, as identified hereinabove.

The present invention also includes many novel transition-metal complexes which are useful oxidation catalysts. Such transition-metal complexes include: Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV), preferably Mn(II), Mn(III), Mn(IV), Fe(II), Fe(III), Cr(II), Cr(III), Cr(IV), Cr(V), and Cr(VI), more preferably the Mn(II), Mn(III), Mn(IV), Mn(V), Fe(II), Fe(III), Fe (IV), Cr(II) and Cr(III) complexes of the cross-bridged tetraazamacrocycles and cross-bridged pentaazamacrocycles; these complexes include those in which the cross-bridging moiety is a C2–C4 alkyl moiety and in which there is a mole ratio of macrocycle to metal of 1:1, and moreover these are most preferably monometallic mononuclear complexes, though in general, dimetallic or multimetallic complexes are not excluded.

To further illustrate, a preferred sub-group of the inventive transition-metal complexes includes the Mn(II), Fe(II) and Cr(III) complexes of the ligand 1.2:

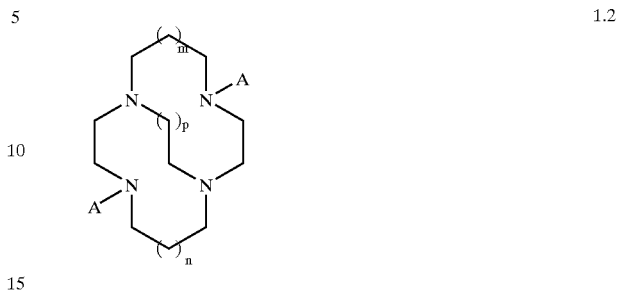

1.2 wherein m and n are integers from 0 to 2, p is an integer from 1 to 6, preferably m and n are both 0 or both 1 (preferably both 1), or m is 0 and n is at least 1; and p is 1; and A is a nonhydrogen moiety preferably having no aromatic content; more particularly each A can vary independently and is preferably selected from methyl, ethyl, propyl, isopropyl, butyl, isobutyl, tert-butyl, C5–C20 alkyl, and one, but not both, of the A moieties is benzyl, and combinations thereof. In one such complex, one A is methyl and one A is benzyl.

All parts, percentages and ratios used herein are expressed as percent weight unless otherwise specified. All documents cited are, in relevant part, incorporated herein by reference.

DETAILED DESCRIPTION OF THE INVENTION

Catalytic Systems for Oxidizing Materials:

The catalytic systems of the present invention comprise a particularly selected transition-metal oxidation catalyst which is a complex of a transition metal and a macropolycyclic rigid ligand, preferably one which is cross-bridged; the catalytic systems preferably also comprise an oxidation agent or "primary oxidant", preferably one which is a low cost, readily available substance producing little or no waste, such as a source of hydrogen peroxide. The source of hydrogen peroxide can be $H_2O_2$ itself, its solutions, or any common hydrogen-peroxide releasing salt, adduct or precursor, such as sodium perborate, sodium percarbonate, or mixtures thereof. Also useful are other sources of available oxygen such as persulfate (e.g., OXONE, manufactured by DuPont), as well as preformed organic peracids and other organic peroxides. More generally, chlorine or other oxidants such as $ClO_2$ or NaOCl can be used.

Mixtures of primary oxidants can be used; in such mixtures, an oxidant which is not present in major proportion can be used, for example as in mixtures of a major proportion of hydrogen peroxide and a minor proportion of peracetic acid or its salts. In this example, the peracetic acid is termed the "secondary oxidant". Secondary oxidants can be selected from the same list of oxidants given hereinafter; the use of secondary oxidants is optional but may be highly desirable in certain embodiments of the invention. The catalytic system often further comprises further adjuncts, including compounds which liberate oxidant as a result of in-situ chemical reaction; as well as solvents and other additives characteristic of the end-use of the catalytic system. To secure the benefits of the invention, a substrate material, such as a chemical compound to be oxidized, or a commercial mixture of materials such as a paper pulp, or a soiled material such as a textile containing one or more materials or soils to be oxidized, is added to the catalytic system under widely ranging conditions further described hereinafter.

The catalytic systems herein are useful for oxidative synthetic chemistry processes, such as oxidation of organic functional groups, hydrocarbons, heteroatoms, and epoxidation (including enantiomeric) of alkenes and enynes, oxidation of sulfides to sulfones, and the like.

The present invention catalytic systems also have utility in the area of oxidizing (preferably including bleaching) wood pulp for use in, for example, paper making processes. Other utilities include oxidative destruction of waste materials or effluents.

Effective Amounts of Catalyst Materials

The term "catalytically effective amount", as used herein, refers to an amount of the transition-metal oxidation catalyst present in the present invention catalytic systems, or during use according to the present invention methods, that is sufficient, under whatever comparative or use conditions are employed, to result in at least partial oxidation of the material sought to be oxidized by the catalytic systems or method. For example, in the synthesis of epoxides from alkenes, the catalytic amount is that amount which is sufficient to catalyze the desired epoxidation reaction. As noted, the invention encompasses catalytic systems both at their in-use levels and at the levels which may commercially be provided for sale as "concentrates"; thus "catalytic systems" herein include both those in which the catalyst is highly dilute and ready to use, for example at ppb levels, and compositions having rather higher concentrations of catalyst and adjunct materials. Intermediate level compositions, as noted in summary, can include those comprising from about 0.01 ppm to about 500 ppm, more preferably from about 0.05 ppm to about 50 ppm, more preferably still from about 0.1 ppm to about 10 ppm of transition-metal catalyst and the balance to 100%, typically about 99% or more, being solid-form or liquid-form adjunct materials (for example fillers, solvents, and adjuncts especially adapted to a particular use, such as papermaking adjuncts, detergent adjuncts, or the like). In terms of amounts of materials, the invention also encompasses a large number of novel transition-metal catalysts per-se, especially including their substantially pure (100% active) forms. Other amounts, for example of oxidant materials and other adjuncts for specialized uses, are illustrated in more detail hereinafter.

Transition-Metal Oxidation Catalysts:

The present invention catalytic systems comprise a transition-metal oxidation catalyst. In general, the catalyst contains an at least partially covalently bonded transition metal, and bonded thereto at least one particularly defined macropolycyclic rigid ligand, preferably one having four or more donor atoms and which is cross-bridged or otherwise tied so that the primary macrocycle ring complexes in a folded conformation about the metal. Catalysts herein are thus neither of the more conventional macrocyclic type: e.g., porphyrin complexes, in which the metal can readily adopt square-planar configuration; nor are they complexes in which the metal is fully encrypted in a ligand. Rather, the presently useful catalysts represent a selection of all the many complexes, hitherto largely unrecognized, which have an intermediate state in which the metal is bound in a "cleft". Further, there can be present in the catalyst one or more additional ligands, of generally conventional type such as chloride covalently bound to the metal; and, if needed, one or more counter-ions, most commonly anions such as chloride, hexafluorophosphate, perchlorate or the like; and additional molecules to complete crystal formation as needed, such as water of crystallization. Only the transition-metal and macropolycyclic rigid ligand are, in general, essential.

Transition-metal oxidation catalysts useful in the invention catalytic systems can in general include known compounds where they conform with the invention definition, as well as, more preferably, any of a large number of novel compounds expressly designed for the present oxidation catalysis uses and non-limitingly illustrated by any of the following:

Dichloro-5,12-dimethyl-1,5,8,12-tetraazabicyclo[6.6.2]hexadecane Manganese(II)

Dichloro-4,10-dimethyl-1,4,7,10-tetraazabicyclo[5.5.2]tetradecane Manganese(II)

Diaquo-5,12-dimethyl-1,5,8,12-tetraazabicyclo[6.6.2]hexadecane Manganese(II) Hexafluorophosphate Aquo-hydroxy-5,12-dimethyl-1,5,8,12-tetraazabicyclo[6.6.2]hexadecane Manganese(III) Hexafluorophosphate Diaquo-4,10-dimethyl-1,4,7,10-tetraazabicyclo[5.5.2]tetradecane Manganese(II) Hexafluorophosphate Diaquo-5,12-dimethyl-1,5,8,12-tetraazabicyclo[6.6.2]hexadecane Manganese(II) Tetrafluoroborate Diaquo-4,10-dimethyl-1,4,7,10-tetraazabicyclo[5.5.2]tetradecane Manganese(II) Tetrafluoroborate Dichloro-5,12-dimethyl-1,5,8,12-tetraazabicyclo[6.6.2]hexadecane Manganese(III) Hexafluorophosphate Dichloro-5,12-di-n-butyl-1,5,8,12-tetraaza-bicyclo[6.6.2]hexadecane Manganese(II)

Dichloro-5,12-dibenzyl-1,5,8,12-tetraazabicyclo[6.6.2]hexadecane Manganese(II)

Dichloro-5-n-butyl-12-methyl-1,5,8,12-tetraaza-bicyclo[6.6.2]hexadecane Manganese(II)

Dichloro-5-n-octyl-12-methyl-1,5,8,12-tetraaza-bicyclo[6.6.2]hexadecane Manganese(II)

Dichloro-5-n-butyl-12-methyl-1,5,8,12-tetraaza-bicyclo[6.6.2]hexadecane Manganese(II)

Dichloro-5,12-dimethyl-1,5,8,12-tetraazabicyclo[6.6.2]hexadecane Iron(II)

Dichloro-4,10-dimethyl-1,4,7,10-tetraazabicyclo[5.5.2]tetradecane Iron(II)

Dichloro-5,12-dimethyl-1,5,8,12-tetraazabicyclo[6.6.2]hexadecane Copper(II)

Dichloro-4,10-dimethyl-1,4,7,10-tetraazabicyclo[5.5.2]tetradecane Copper(II)

Dichloro-5,12-dimethyl-1,5,8,12-tetraazabicyclo[6.6.2]hexadecane Cobalt(II)

Dichloro-4,10-dimethyl-1,4,7,10-tetraazabicyclo[5.5.2]tetradecane Cobalt(II)

Dichloro 5,12-dimethyl—4-phenyl-1,5,8,12-tetraazabicyclo[6.6.2]hexadecane Manganese (II)

Dichloro-4,10-dimethyl-3-phenyl-1,4,7,10-tetraazabicyclo[5.5.2]tetradecane Manganese(II)

Dichloro-5,12-dimethyl-4,9-diphenyl-1,5,8,12-tetraazabicyclo[6.6.2]hexadecane Manganese(II)

Dichloro-4,10-dimethyl-3,8-diphenyl-1,4,7,10-tetraazabicyclo[5.5.2]tetradecane Manganese(II)

Dichloro-5,12-dimethyl-2,11-diphenyl-1,5,8,12-tetraazabicyclo[6.6.2]hexadecane Manganese(II)

Dichloro-4,10-dimethyl-4,9-diphenyl-1,4,7,10-tetraazabicyclo[5.5.2]tetradecane Manganese(II)

Dichloro-2,4,5,9,11,12-hexamethyl-1,5,8,12-tetraazabicyclo[6.6.2]hexadecane Manganese(II)

Dichloro-2,3,5,9,10,12-hexamethyl-1,5,8,12-tetraazabicyclo[6.6.2]hexadecane Manganese(II)

Dichloro-2,2,4,5,9,9,11,12-octamethyl-1,5,8,12-tetraazabicyclo[6.6.2]hexadecane Manganese (II)

Dichloro-2,2,4,5,9,11,11,12-octamethyl-1,5,8,12-tetraazabicyclo[6.6.2]hexadecane Manganese(II)

Dichloro-3,3,5,10,10,12-hexamethyl-1,5,8,12-tetraazabicyclo[6.6.2]hexadecane Manganese (II)

Dichloro-3,5,10,12-tetramethyl-1,5,8,12-tetraazabicyclo[6.6.2]hexadecane Manganese (II)
Dichloro-3-butyl-5,10,12-trimethyl-1,5,8,12-tetraazabicyclo[6.6.2]hexadecane Manganese (II)
Dichloro-1,5,8,12-tetraazabicyclo[6.6.2]hexadecane Manganese(II)
Dichloro-1,4,7,10-tetraazabicyclo[5.5.2]tetradecane Manganese(II)
Dichloro-1,5,8,12-tetraazabicyclo[6.6.2]hexadecane Iron (II)
Dichloro-1,4,7,10-tetraazabicyclo[5.5.2]tetradecane Iron(II)
Aquo-chloro-2-(2-hydroxyphenyl)-5,12-dimethyl1,5,8,12-tetraazabicyclo[6.6.2]hexadecane Manganese(II)
Aquo-chloro-10-(2-hydroxybenzyl)-4,10-dimethyl-1,4,7,10-tetraazabicyclo[5.5.2]tetradecane Manganese(II)
Chloro-2-(2-hydroxybenzyl)-5-methyl1,5,8,12-tetraazabicyclo[6.6.2]hexadecane Manganese(II)
Chloro-10-(2-hydroxybenzyl)-4-methyl-1,4,7,10-tetraazabicyclo[5.5.2]tetradecane Manganese(II)
Chloro-5-methyl-12-(2-picolyl)-1,5,8,12-tetraazabicyclo[6.6.2]hexadecane Manganese(II) Chloride
Chloro-4-methyl-10-(2-picolyl)-1,4,7,10-tetraazabicyclo[5.5.2]tetradecane Manganese(II) Chloride
Dichloro-5-(2-sulfato)dodecyl-12-methyl-1,5,8,12-tetraazabicyclo[6.6.2]hexadecane Manganese(III)
Aquo-Chloro-5-(2-sulfato)dodecyl-12-methyl-1,5,8,12-tetraazabicyclo[6.6.2]hexadecane Manganese(II)
Aquo-Chloro-5-(3-sulfonopropyl)-12-methyl-1,5,8,12-tetraazabicyclo[6.6.2]hexadecane Manganese(II)
Dichloro-5-(Trimethylammoniopropyl)dodecyl-12-methyl-1,5,8,12-tetraazabicyclo[6.6.2]hexadecane Manganese (III) Chloride
Dichloro-5,12-dimethyl-1,4,7,10,13-pentaazabicyclo[8.5.2]heptadecane Manganese(II)
Dichloro-14,20-dimethyl-1,10,14,20-tetraazatriyclo[8.6.6]docosa-3(8),4,6-triene Manganese(II)
Dichloro-4,11-dimethyl-1,4,7,11-tetraazabicyclo[6.5.2]pentadecane Manganese(II)
Dichloro-5,12-dimethyl-1,5,8,12-tetraazabicyclo[7.6.2]heptadecane Manganese(II)
Dichloro-5,13-dimethyl-1,5,9,13-tetraazabicyclo[7.7.2]heptadecane Manganese(II)
Dichloro-3,10-bis(butylcarboxy)-5,12-dimethyl-1,5,8,12-tetraazabicyclo[6.6.2]hexadecane Manganese(II)
Diaquo-3,10-dicarboxy-5,12-dimethyl-1,5,8,12-tetraazabicyclo[6.6.2]hexadecane Manganese(II)
Chloro-20-methyl-1,9,20,24,25-pentaaza-tetracyclo[7.7.7.1$^{3,7}$.1$^{11,15}$.]pentacosa-3,5,7(24),11,13,15(25)-hexaene manganese(II) Hexafluorophosphate
Trifluoromethanesulfono-20-methyl-1,9,20,24,25-pentaaza-tetracyclo[7.7.7.1$^{3,7}$.1$^{11,15}$.]pentacosa-3,5,7(24),11,13,15(25)-hexaene Manganese(II) Trifluoromethanesulfonate
Trifluoromethanesulfono-20-methyl-1,9,20,24,25-pentaaza-tetracyclo[7.7.7.1$^{3,7}$.1$^{11,15}$.]pentacosa-3,5,7(24),11,13,15(25)-hexaene Iron(II) Trifluoromethanesulfonate
Chloro-5,12,17-trimethyl-1,5,8,12,17-pentaazabicyclo[6.6.5]nonadecane Manganese(II) Hexafluorophosphate
Chloro-4,10,15-trimethyl-1,4,7,10,15-pentaazabicyclo[5.5.5]heptadecane Manganese(II) Hexafluorophosphate
Chloro-5,12,17-trimethyl-1,5,8,12,17-pentaazabicyclo[6.6.5]nonadecane Manganese(II) Chloride
Chloro-4,10,15-trimethyl-1,4,7,10,15-pentaazabicyclo[5.5.5]heptadecane Manganese(II) Chloride Preferred complexes useful as transition-metal oxidation catalysts more generally include not only monometallic, mononuclear kinds such as those illustrated hereinabove but also bimetallic, trimetallic or cluster kinds, especially when the polymetallic kinds transform chemically in the presence of a primary oxidant to form a mononuclear, monometallic active species. Monometallic, mononuclear complexes are preferred. As defined herein, a monometallic transition-metal oxidation catalyst contains only one transition metal atom per mole of complex. A monometallic, mononuclear complex is one in which any donor atoms of the essential macrocyclic ligand are bonded to the same transition metal atom, that is, the essential ligand does not "bridge" across two or more transition-metal atoms.

Transition Metals of the Catalyst

Just as the macropolycyclic ligand cannot vary indeterminately for the present useful purposes, nor can the metal. An important part of the invention is to arrive at a match between ligand selection and metal selection which results in excellent oxidation catalysis. In general, transition-metal oxidation catalysts herein comprise a transition metal selected from the group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV).

Preferred transition-metals in the instant transition-metal oxidation catalyst include manganese, iron and chromium. Preferred oxidation states include the (II) and (III) oxidation states. Manganese(II) in both the low-spin configuration and high spin complexes are included. It is to be noted that complexes such as low-spin Mn(II) complexes are rather rare in all of coordination chemistry. The designation (II) or (III) denotes a coordinated transition metal having the requisite oxidation state; the coordinated metal atom is not a free ion or one having only water as a ligand.

Ligands

In general, as used herein, a "ligand" is any moiety capable of direct covalent bonding to a metal ion. Ligands can be charged or neutral and may range widely, including simple monovalent donors, such as chloride, or simple amines which form a single coordinate bond and a single point of attachment to a metal; to oxygen or ethylene, which can form a three-membered ring with a metal and thus can be said to have two potential points of attachment, to larger moieties such as ethylenediamine or aza macrocycles, which form up to the maximum number of single bonds to one or more metals that are allowed by the available sites on the metal and the number of lone pairs or alternate bonding sites of the free ligand. Numerous ligands can form bonds other than simple donor bonds, and can have multiple points of attachment.

Ligands useful herein can fall into several groups: the essential macropolycyclic rigid ligand, preferably a cross-bridged macropolycycle (preferably there will be one such ligand in a useful transition-metal complex, but more, for example two, can be present, but not in preferred mononuclear complexes); other, optional ligands, which in general are different from the essential cross-bridged macropolycycle (generally there will be from 0 to 4, preferably from 1 to 3 such ligands); and ligands associated transiently with the metal as part of the catalytic cycle, these latter typically being related to water, hydroxide, oxygen, water, hydroxide, or peroxides. Ligands of the third group are not essential for defining the metal oxidation catalyst, which is a stable, isolable chemical compound that can be fully characterized. Ligands which bind to metals through donor atoms each having at least a single lone pair of electrons available for donation to a metal have a donor capability, or potential denticity, at least equal to the number of donor atoms. In general, that donor capability may be fully or only partially exercised.

Macropolycyclic Rigid Ligands

To arrive at the instant transition-metal catalysts, a macropolycyclic rigid ligand is essential. This is coordinated (covalently connected to any of the above-identified transition-metals) by at least three, preferably at least four, and most preferably four or five, donor atoms to the same transition metal.

Generally, the macropolycyclic rigid ligands herein can be viewed as the result of imposing additional structural rigidity on specifically selected "parent macrocycles". The term "rigid" herein has been defined as the constrained converse of flexibility: see D. H. Busch., *Chemical Reviews.*, (1993), 93, 847–860, incorporated by reference. More particularly, "rigid" as used herein means that the essential ligand, to be suitable for the purposes of the invention, must be determinably more rigid than a macrocycle ("parent macrocycle") which is otherwise identical (having the same ring size and type and number of atoms in the main ring) but lacks the superstructure (especially linking moieties or, preferably cross-bridging moieties) of the present ligands. In determining the comparative rigidity of the macrocycles with and without superstructures, the practitioner will use the free form (not the metal-bound form) of the macrocycles. Rigidity is well-known to be useful in comparing macrocycles; suitable tools for determining, measuring or comparing rigidity include computational methods (see, for example, Zimmer, *Chemical Reviews*, (1995), 95(38), 2629–2648 or Hancock et al., *Inorganica Chimica Acta*, (1989), 164, 73–84. A determination of whether one macrocycle is more rigid than another can be often made by simply making a molecular model, thus it is not in general essential to know configurational energies in absolute terms or to precisely compute them. Excellent comparative determinations of rigidity of one macrocycle vs. another can be made using inexpensive personal computer-based computational tools, such as ALCHEMY III, commercially available from Tripos Associates. Tripos also has available more expensive software permitting not only comparative, but absolute determinations; alternately, SHAPES can be used (see Zimmer cited supra). One observation which is significant in the context of the present invention is that there is an optimum for the present purposes when the parent macrocycle is distinctly flexible as compared to the cross-bridged form. Thus, unexpectedly, it is preferred to use parent macrocycles containing at least four donor atoms, such as cyclam derivatives, and to cross-bridge them, rather than to start with a more rigid parent macrocycle. Another observation is that cross-bridged macrocycles are significantly preferred over macrocycles which are bridged in other manners.

The macrocyclic rigid ligands herein are of course not limited to being synthesized from any preformed macrocycle plus preformed "rigidizing" or "conformation-modifying" element: rather, a wide variety of synthetic means, such as template syntheses, are useful. See for example Busch et al., reviewed in "Heterocyclic compounds: Aza-crown macrocycles", J. S. Bradshaw et. al., referred to in the Background Section hereinbefore, for synthetic methods.

In one aspect of the present invention, the macropolycyclic rigid ligands herein include those comprising:

(i) an organic macrocycle ring containing three, preferably four, or more donor atoms (preferably at least 3, more preferably at least 4, of these donor atoms are N) separated from each other by covalent linkages of at least one, preferably 2 or 3, non-donor atoms, two to five (preferably three to four, more preferably four) of these donor atoms being coordinated to the same transition metal in the complex; and (ii) a linking moiety, preferably a cross-bridging chain, which covalently connects at least 2 (preferably non-adjacent) donor atoms of the organic macrocycle ring, said covalently connected (preferably non-adjacent) donor atoms being bridgehead donor atoms which are coordinated to the same transition metal in the complex, and wherein said linking moiety (preferably a cross-bridged chain) comprises from 2 to about 10 atoms (preferably the cross-bridged chain is selected from 2, 3 or 4 non-donor atoms, and 4–6 non-donor atoms with a further donor atom).

While clear from the various contexts and illustrations already presented, the practitioner may further benefit if certain terms receive additional definition and illustration. As used herein, "macrocyclic rings" are covalently connected rings formed from three or more, preferably four or more, donor atoms (i.e., heteroatoms such as nitrogen or oxygen) with carbon chains connecting them, and any macrocycle ring as defined herein must contain a total of at least ten, preferably at least twelve, atoms in the macrocycle ring. A macropolycyclic rigid ligand herein may contain more than one ring of any sort per ligand, but at least one macrocycle ring must be identifiable. Moreover, in the preferred embodiments, no two hetero-atoms are directly connected. Preferred transition-metal oxidation catalysts are those wherein the macropolycyclic rigid ligand comprises an organic macrocycle ring (main ring) containing at least 10–20 atoms, preferably 12–18 atoms, more preferably from about 12 to about 20 atoms, most preferably 12 to 16 atoms.

"Donor atoms" herein are heteroatoms such as nitrogen, oxygen, phosphorus or sulfur, which when incorporated into a ligand still have at least one lone pair of electrons available for forming a donor-acceptor bond with a metal. Preferred transition-metal oxidation catalyst are those wherein the donor atoms in the organic macrocycle ring of the cross-bridged macropolycyclic ligand are selected from the group consisting of N, O, S, and P, preferably N and O, and most preferably all N. Also preferred are cross-bridged macropolycyclic ligands comprising 4 or 5 donor atoms, all of which are coordinated to the same transition metal. Most preferred transition-metal oxidation catalysts are those wherein the cross-bridged macropolycyclic ligand comprises 4 nitrogen donor atoms all coordinated to the same transition metal, and those wherein the cross-bridged macropolycyclic ligand comprises 5 nitrogen atoms all coordinated to the same transition metal.

"Non-donor atoms" of the macropolycyclic rigid ligand herein are most commonly carbon, though a number of atom types can be included, especially in optional exocyclic substituents (such as "pendant" moieties, illustrated hereinafter) of the macrocycles, which are neither donor atoms for purposes essential to form the metal catalysts, nor are they carbon. Thus, in the broadest sense, the term "non-donor atoms" can refer to any atom not essential to forming donor bonds with the metal of the catalyst. Examples of such atoms could include heteroatoms such as sulfur as incorporated in a non-coordinatable sulfonate group, phosphorus as incorporated into a phosphonium salt moiety, phosphorus as incorporated into a P(V) oxide, a non-transition metal, or the like. In certain preferred embodiments, all non-donor atoms are carbon.

The term "macropolycyclic ligand" is used herein to refer to the essential ligand required for forming the essential metal catalyst. As indicated by the term, such a ligand is both a macrocycle and is polycyclic. "Polycyclic" means at least bicyclic in the conventional sense. The essential macropolycyclic ligands must be rigid, and preferred ligands must also cross-bridged.

Non-limiting examples of macropolycyclic rigid ligands, as defined herein, include 1.3–1.7:

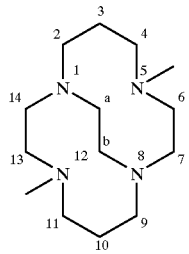

1.3

Ligand 1.3 is a macropolycylic rigid ligand in accordance with the invention which is a highly preferred, cross-bridged, methyl-substituted (all nitrogen atoms tertiary) derivative of cyclam. Formally, this ligand is named 5,12-dimethyl-1,5,8,12-tetraazabicyclo[6.6.2]hexadecane using the extended von Baeyer system. See "A Guide to IUPAC Nomenclature of Organic Compounds: Recommendations 1993", R. Panico, W. H. Powell and J-C Richer (Eds.), Blackwell Scientific Publications, Boston, 1993; see especially section R-2.4.2.1. According to conventional terminology, N1 and N8 are "bridgehead atoms"; as defined herein, more particularly "bridgehead donor atoms" since they have lone pairs capable of donation to a metal. N1 is connected to two non-bridgehead donor atoms, N5 and N12, by distinct saturated carbon chains 2, 3, 4 and 14, 13 and to bridgehead donor atom N8 by a "linking moiety" a,b which here is a saturated carbon chain of two carbon atoms. N8 is connected to two non-bridgehead donor atoms, N5 and N12, by distinct chains 6, 7 and 9, 10, 11. Chain a,b is a "linking moiety" as defined herein, and is of the special, preferred type referred to as a "cross-bridging" moiety. The "macrocyclic ring" of the ligand supra, or "main ring" (IUPAC), includes all four donor atoms and chains 2, 3, 4; 6, 7; 9, 10, 11 and 13, 14 but not a,b. This ligand is conventionally bicyclic. The short bridge or "linking moiety" a,b is a "cross-bridge" as defined herein, with a,b bisecting the macrocyclic ring.

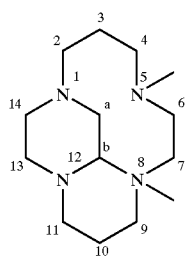

1.4

Ligand 1.4 lies within the general definition of macropolycyclic rigid ligands as defined herein, but is not a preferred ligand since it is not "cross-bridged" as defined herein. Specifically, the "linking moiety" a,b connects "adjacent" donor atoms N1 and N12, which is outside the preferred embodiment of the present invention: see for comparison the preceding macrocyclic rigid ligand, in which the linking moiety a,b is a cross-bridging moiety and connects "non-adjacent" donor atoms.

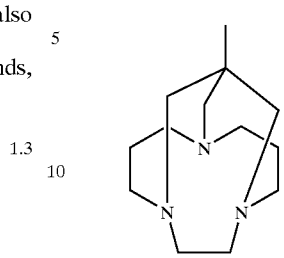

1.5

Ligand 1.5 lies within the general definition of macropolycyclic rigid ligands as defined herein, but is not a preferred ligand since it contains only three donor atoms, all of which are bridgehead donor atoms.

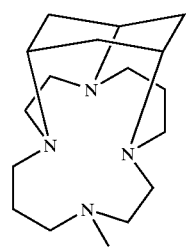

1.6

Ligand 1.6 lies within the general definition of macropolycylic rigid ligands as defined herein. This ligand can be viewed as a "main ring" which is a tetraazamacrocycle having three bridgehead donor atoms. This macrocycle is bridged by a "linking moiety" having a structure more complex than a simple chain, containing as it does a secondary ring. The linking moiety includes both a "cross-bridging" mode of bonding, and a non-cross-bridging mode.

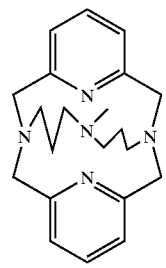

1.7

Ligand 1.7 lies within the general definition of macropolycylic rigid ligands. Five donor atoms are present; two being bridgehead donor atoms. This ligand is a preferred cross-bridged ligand. It contains no exocyclic or pendant substituents which have aromatic content.

In contrast, for purposes of comparison, the following ligands (1.8 and 1.9) conform neither with the broad definition of macropolycyclic rigid ligands in the present invention, nor with the preferred cross-bridged sub-family thereof and therefore are completely outside the present invention

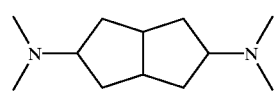

1.8

In the ligand supra, neither nitrogen atom is a bridgehead donor atom. There are insufficient donor atoms.

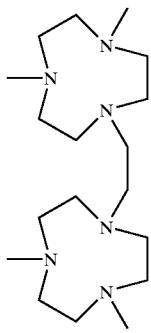

1.9

The ligand supra is also outside the present invention. The nitrogen atoms are not bridgehead donor atoms, and the two-carbon linkage between the two main rings does not meet the invention definition of a "linking moiety" since, instead of linking across a single macrocycle ring, it links two different rings. The linkage therefore does not confer rigidity as used in the term "macropolycyclic rigid ligand". See the definition of "linking moiety" hereinafter.

Generally, the essential macropolycyclic rigid ligands (and the corresponding transition-metal catalysts) herein comprise:
(a) at least one macrocycle main ring comprising three or more heteroatoms; and
(b) a covalently connected non-metal superstructure capable of increasing the rigidity of the macrocycle, preferably selected from
(i) a bridging superstructure, such as a linking moiety;
(ii) a cross-bridging superstructure, such as a cross-bridging linking moiety; and
(iii) combinations thereof.

The term "superstructure" is used herein as defined by Busch et al., in the Chemical Reviews article incorporated hereinabove.

Preferred superstructures herein not only enhance the rigidity of the parent macrocycle, but also favor folding of the macrocycle so that it co-ordinates to a metal in a cleft. Suitable superstructures can be remarkably simple, for example a linking moiety such as any of those illustrated in 1.10 and 1.11 below, can be used.

1.10 wherein n is an integer, for example from 2 to 8, preferably less than 6, typically 2 to 4, or

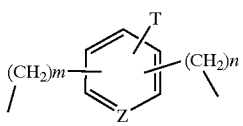

1.11 wherein m and n are integers from about 1 to 8, more preferably from 1 to 3; Z is N or CH; and T is a compatible substituent, for example H, alkyl, trialkylammonium, halogen, nitro, sulfonate, or the like. The aromatic ring in 1.11 can be replaced by a saturated ring, in which the atom in Z connecting into the ring can contain N, O, S or C.

Without intending to be limited by theory, it is believed that the preorganization built into the macropolycyclic ligands herein that leads to extra kinetic and/or thermodynamic stability of their metal complexes arises from either or both of topological constraints and enhanced rigidity (loss of flexibility) compared to the free parent macrocycle which has no superstructure. The macropolycyclic rigid ligands as defined herein and their preferred cross-bridged sub-family, which can be said to be "ultra-rigid", combine two sources of fixed preorganization. In preferred ligands herein, the linking moieties and parent macrocycle rings are combined to form ligands which have a significant extent of "fold", typically greater than in many known superstructured ligands in which a superstructure is attached to a largely planar, often unsaturated macrocycle. See, for example, : D. H. Busch, *Chemical Reviews*, (1993), 93, 847–880. Further, the preferred ligands herein have a number of particular properties, including (1) they are characterized by very high proton affinities, as in so-called "proton sponges"; (2) they tend to react slowly with multivalent transition metals, which when combined with (1) above, renders synthesis of their complexes with certain hydrolyzable metal ions difficult in hydroxylic solvents; (3) when they are coordinated to transition metal atoms as identified herein, the ligands result in complexes that have exceptional kinetic stability such that the metal ions only dissociate extremely slowly under conditions that would destroy complexes with ordinary ligands; and (4) these complexes have exceptional thermodynamic stability; however, the unusual kinetics of ligand dissociation from the transition metal may defeat conventional equilibrium measurements that might quantitate this property.

Other usable but more complex superstructures suitable for the present invention purposes include those containing an additional ring, such as in 1.6. Other bridging superstructures when added to a macrocycle include, for example, 1.4. In contrast, cross-bridging superstructures unexpectedly produce a substantial improvement in the utility of a macrocyclic ligand for use in oxidation catalysis: a preferred cross-bridging superstructure is 1.3. A superstructure illustrative of a bridging plus cross-bridging combination is 1.12:

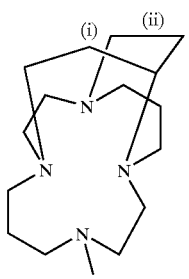

1.12

In 1.12, linking moiety (i) is cross-bridging, while linking moiety (ii) is not. 1.12 is less preferred than 1.3.

More generally, a "linking moiety", as defined herein, is a covalently linked moiety comprising a plurality of atoms which has at least two points of covalent attachment to a macrocycle ring and which does not form part of the main ring or rings of the parent macrocycle. In other terms, with the exception of the bonds formed by attaching it to the parent macrocycle, a linking moiety is wholly in a superstructure.

The terms "cross-bridged" or "cross-bridging", as used herein, refers to covalent ligation, bisection or "tying" of a macrocycle ring in which two donor atoms of the macrocycle ring are covalently connected by a linking moiety, for example an additional chain distinct from the macrocycle ring, and further, preferably, in which there is at least one donor atom of the macrocycle ring in each of the sections of the macrocycle ring separated by the ligation, bisection or tying. Cross-bridging is not present in structure 1.4 hereinabove; it is present in 1.3, where two donor atoms of a preferred macrocycle ring are connected in such manner that there is not a donor atom in each of the bisection rings. Of course, provided that cross-bridging is present, any other kind of bridging can optionally be added and the bridged macrocycle will retain the preferred property of being "cross-bridged": see Structure 1.12. A "cross-bridged chain" or "cross-bridging chain", as defined herein, is thus a highly preferred type of linking moiety comprising a plurality of atoms which has at least two points of covalent attachment to a macrocycle ring and which does not form part of the original macrocycle ring (main ring), and further, which is connected to the main ring using the rule identified in defining the term "cross-bridging".

The term "adjacent" as used herein in connection with donor atoms in a macrocycle ring means that there are no donor atoms intervening between a first donor atom and another donor atom within the macrocycle ring; all intervening atoms in the ring are non-donor atoms, typically they are carbon atoms. The complementary term "non-adjacent" as used herein in connection with donor atoms in a macrocycle ring means that there is at least one donor atom intervening between a first donor atom and another that is being referred to. In preferred cases such as a cross-bridged tetraazamacrocycle, there will be at least a pair of non-adjacent donor atoms which are bridgehead atoms, and a further pair of non-bridgehead donor atoms.

"Bridgehead" atoms herein are atoms of a macropolycyclic ligand which are connected into the structure of the macrocycle in such manner that each non-donor bond to such an atom is a covalent single bond and there are sufficient covalent single bonds to connect the atom termed "bridgehead" such that it forms a junction of at least two rings, this number being the maximum observable by visual inspection in the un-coordinated ligand.

In general, the metal oxidation catalysts herein may contain bridgehead atoms which are carbon, however, and importantly, in certain preferred embodiments, all essential bridgehead atoms are heteroatoms, all heteroatoms are tertiary, and further, they each co-ordinate through lone pair donation to the metal. Thus, bridgehead atoms are junction points not only of rings in the macrocycle, but also of chelate rings.

The term "a further donor atom" unless otherwise specifically indicated, as used herein, refers to a donor atom other than a donor atom contained in the macrocycle ring of an essential macropolycycle. For example, a "further donor atom" may be present in an optional exocyclic substituent of a macrocyclic ligand, or in a cross-bridged chain thereof. In certain preferred embodiments, a "further donor atom" is present only in a cross-bridged chain.

The term "coordinated with the same transition metal" as used herein is used to emphasize that a particular donor atom or ligand does not bind to two or more distinct metal atoms, but rather, to only one.

Optional Ligands

It is to be recognized for the transition-metal oxidation catalysts useful in the present invention catalytic systems that additional non-macropolycyclic ligands may optionally also be coordinated to the metal, as necessary to complete the coordination number of the metal complexed. Such ligands may have any number of atoms capable of donating electrons to the catalyst complex, but preferred optional ligands have a denticity of 1 to 3, preferably 1. Examples of such ligands are $H_2O$, $ROH$, $NR_3$, $RCN$, $OH^-$, $OOH^-$, $RS^-$, $RO^-$, $RCOO^-$, $OCN^-$, $SCN^-$, $N_3^-$, $CN^-$, $F^-$, $Cl^-$, $Br^-$, $I^-$, $O_2^-$, $NO_3^-$, $NO_2^-$, $SO_4^{2-}$, $SO_3^{2-}$, $PO_4^{3-}$, organic phosphates, organic phosphonates, organic sulfates, organic sulfonates, and aromatic N donors such as pyridines, pyrazines, pyrazoles, imidazoles, benzimidazoles, pyrimidines, triazoles and thiazoles with R being H, optionally substituted alkyl, optionally substituted aryl. Preferred transition-metal oxidation catalysts comprise one or two non-macropolycyclic ligands.

The term "non-macropolycyclic ligands" is used herein to refer to ligands such as those illustrated immediately hereinabove which in general are not essential for forming the metal catalyst, and are not cross-bridged macropolycycles. "Not essential", with reference to such non-macropolycyclic ligands means that, in the invention as broadly defined, they can be substituted by a variety of common alternate ligands. In highly preferred embodiments in which metal, macropolycyclic and non-macropolycyclic ligands are finely tuned into a transition-metal oxidation catalyst, there may of course be significant differences in performance when the indicated non-macropolycyclic ligand(s) are replaced by further, especially non-illustrated, alternative ligands.

The term "metal catalyst" or "transition-metal oxidation catalyst" is used herein to refer to the essential catalyst compound of the invention and is commonly used with the "metal" qualifier unless absolutely clear from the context. Note that there is a disclosure hereinafter pertaining specifically to optional catalyst materials. Therein the term "bleach catalyst" may be used unqualified to refer to optional, organic (metal-free) catalyst materials, or to optional metal-containing catalysts that lack the advantages of the essential catalyst: such optional materials, for example, include known metal porphyrins or metal-containing photobleaches. Other optional catalytic materials herein include enzymes.

The macropolycyclic rigid ligands of the inventive compositions and methods also include ligands selected from the group consisting of:

(i) the macropolycyclic rigid ligand of formula (I) having denticity of 3 or, preferably, 4:

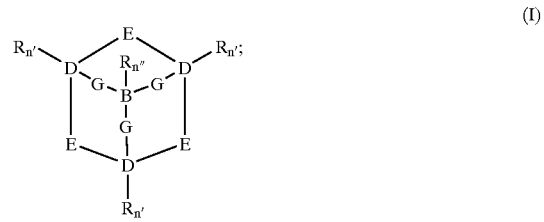

(I)

(ii) the macropolycyclic rigid ligand of formula (II) having denticity of 4 or 5:

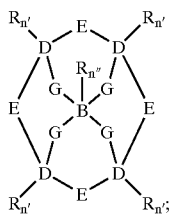

(II)

(iii) the macropolycyclic rigid ligand of formula (III) having denticity of 5 or 6:

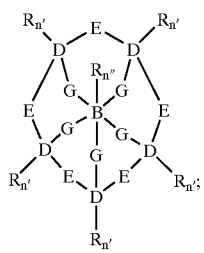

(III)

(iv) the macropolycyclic rigid ligand of formula (IV) having denticity of 6 or 7:

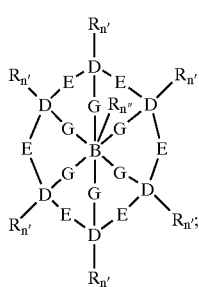

(IV)

wherein in these formulas:
each "E" is the moiety $(CR_n)_a-X-(CR_n)_{a'}$, wherein X is selected from the group consisting of O, S, NR and P, or a covalent bond, and preferably X is a covalent bond and for each E the sum of a+a' is independently selected from 1 to 5, more preferably 2 and 3;
each "G" is the moiety $(CR_n)_b$;
each "R" is independently selected from H, alkyl, alkenyl, alkynyl, aryl, alkylaryl (e.g., benzyl), and heteroaryl, or two or more R are covalently bonded to form an aromatic, heteroaromatic, cycloalkyl, or heterocycloalkyl ring;
each "D" is a donor atom independently selected from the group consisting of N, O, S, and P, and at least two D atoms are bridgehead donor atoms coordinated to the transition metal;
"B" is a carbon atom or "D" donor atom, or a cycloalkyl or heterocyclic ring;
each "n" is an integer independently selected from 1 and 2, completing the valence of the carbon atoms to which the R moieties are covalently bonded;
each "n'" is an integer independently selected from 0 and 1, completing the valence of the D donor atoms to which the R moieties are covalently bonded;
each "n''" is an integer independently selected from 0, 1, and 2 completing the valence of the B atoms to which the R moieties are covalently bonded;

each "a" and "a'" is an integer independently selected from 0–5, preferably a+a' equals 2 or 3, wherein the sum of all "a" plus "a'" in the ligand of formula (I) is within the range of from about 7 to about 12, the sum of all "a" plus "a'" in the ligand of formula (II) is within the range of from about 6 (preferably 8) to about 12, the sum of all "a" plus "a'" in the ligand of formula (III) is within the range of from about 8 (preferably 10) to about 15, and the sum of all "a" plus "a'" in the ligand of formula (IV) is within the range of from about 10 (preferably 12) to about 18;
each "b" is an integer independently selected from 0–5, or in any of the above formulas, one or more of the $(CR_n)_b$ moieties covalently bonded from any D to the B atom is absent as long as at least two $(CR_n)_b$ covalently bond two of the D donor atoms to the B atom in the formula, and the sum of all "b" is within the range of from about 1 to about 5. Preferred ligands of the above formulas are those which are cross-bridged macropolycyclic ligands having Formulas (II), (III) or (IV).

It is to be noted herein that for the above formulas wherein "a" or "a'" is 1, these ligands are not preferred for potential instability reasons in selected solvents, but are still within the scope of the present invention.

Preferred are the transition-metal oxidation catalysts wherein in the cross-bridged macropolycyclic ligand the D and B are selected from the group consisting of N and O, and preferably all D are N. Also preferred are wherein in the cross-bridged macropolycyclic ligand all "a" are independently selected from the integers 2 and 3, all X are selected from covalent bonds, all "a'" are 0, and all "b" are independently selected from the integers 0, 1, and 2. Tetradentate and pentadentate cross-bridged macropolycyclic ligands are most preferred.

Unless otherwise specified, the convention herein when referring to denticity, as in "the macropolycycle has a denticity of four" will be to refer to a characteristic of the ligand: namely, the maximum number of donor bonds that it is capable of forming when it coordinates to a metal. Such a ligand is identified as "tetradentate". Similarly, a macropolycycle containing five nitrogen atoms each with a lone pair is referred to as "pentadentate". The present invention encompasses catalytic systems in which the macrocyclic rigid ligand exerts its full denticity, as stated, in the transition-metal catalyst complexes; moreover, the invention also encompasses any equivalents which can be formed, for example, if one or more donor sites are not directly coordinated to the metal. This can happen, for example, when a pentadentate ligand coordinates through four donor atoms to the transition metal and one donor atom is protonated.

The further to illustrate preferred catalytic systems, the invention also includes those containing metal catalysts wherein the cross-bridged macropolycyclic ligand is a bicyclic ligand; preferably the cross-bridged macropolycyclic ligand is a macropolycyclic moiety of formula (II) having the formula:

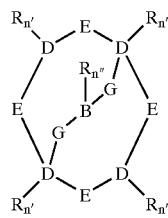

wherein each "a" is independently selected from the integers 2 or 3, and each "b" is independently selected from the integers 0, 1 and 2.

Further preferred are the compositions containing cross-bridged macropoly-cyclic ligands having the formula:

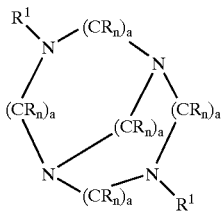

wherein in this formula:
each "n" is an integer independently selected from 1 and 2, completing the valence of the carbon atom to which the R moieties are covalently bonded;
each "R" and "$R^1$" is independently selected from H, alkyl, alkenyl, alkynyl, aryl, alkylaryl (e.g., benzyl) and heteroaryl, or R and/or $R^1$ are covalently bonded to form an aromatic, heteroaromatic, cycloalkyl, or heterocycloalkyl ring, and wherein preferably all R are H and $R^1$ are independently selected from linear or branched, substituted or unsubstituted $C_1$–$C_{20}$ alkyl, alkenyl or alkynyl;
each "a" is an integer independently selected from 2 or 3;
preferably all nitrogen atoms in the cross-bridged macropolycycle rings are coordinated with the transition metal.

The invention further includes the novel methods, compositions, and transition-metal catalysts which include the transition-metal complexes, preferably the Mn, Fe and Cr complexes, or preferred cross-bridged macropolycyclic ligands having the formula:

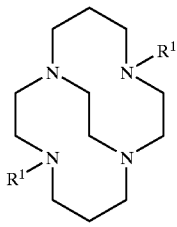

wherein in this formula "$R^1$" is independently selected from H, and linear or branched, substituted or unsubstituted $C_1$–$C_{20}$ alkyl, alkylaryl, alkenyl or alkynyl, more preferably $R^1$ is alkyl or alkylaryl; and preferably all nitrogen atoms in the macropolycyclic rings are coordinated with the transition metal.

Also preferred are cross-bridged macropolycyclic ligands having the formula:

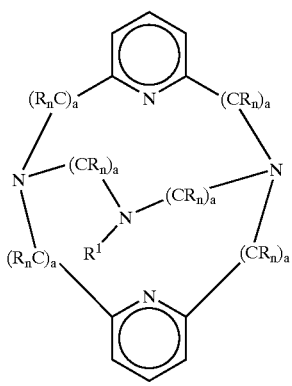

wherein in this formula:
each "n" is an integer independently selected from 1 and 2, completing the valence of the carbon atom to which the R moieties are covalently bonded;

each "R" and "$R^1$" is independently selected from H, alkyl, alkenyl, alkynyl, aryl, alkylaryl (e.g., benzyl), and heteroaryl, or R and/or $R^1$ are covalently bonded to form an aromatic, heteroaromatic, cycloalkyl, or heterocycloalkyl ring, and wherein preferably all R are H and $R^1$ are independently selected from linear or branched, substituted or unsubstituted $C_1$–$C_{20}$ alkyl, alkenyl or alkynyl;
each "a" is an integer independently selected from 2 or 3;
preferably all nitrogen atoms in the macropolycyclic rings are coordinated with the transition metal. In terms of the present invention, even though any of such ligands are known, the invention encompasses the use of these ligands in the form of their transition-metal complexes as oxidation catalysts, or in the form of the defined catalytic systems.

In like manner, included in the definition of the preferred cross-bridged macropolycyclic ligands are those having the formula:

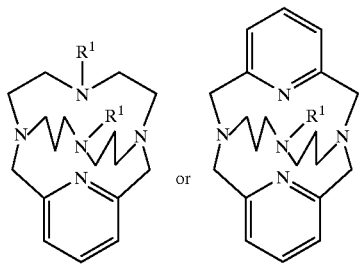

wherein in either of these formulae, "$R^1$" is independently selected from H, or, preferably, linear or branched, substituted or unsubstituted $C_1$–$C_{20}$ alkyl, alkenyl or alkynyl; and preferably all nitrogen atoms in the macropolycyclic rings are coordinated with the transition metal.

The present invention has numerous variations and alternate embodiments which do not depart from its spirit and scope. Thus, in the foregoing catalytic systems, the macropolycyclic ligand can be replaced by any of the following:

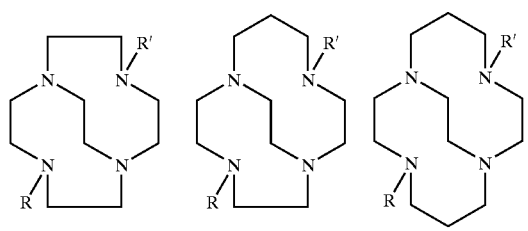
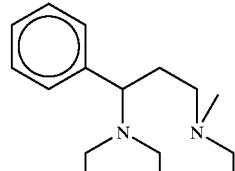
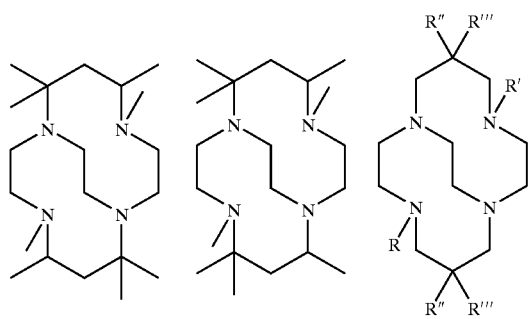
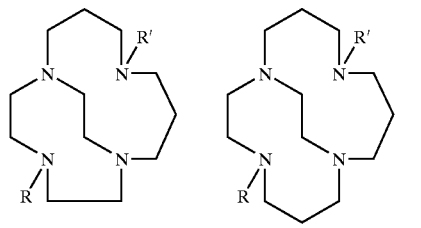
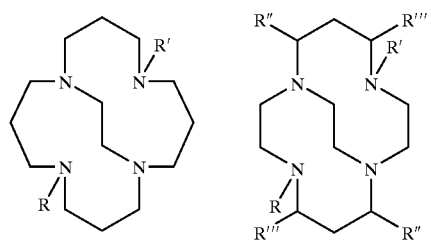
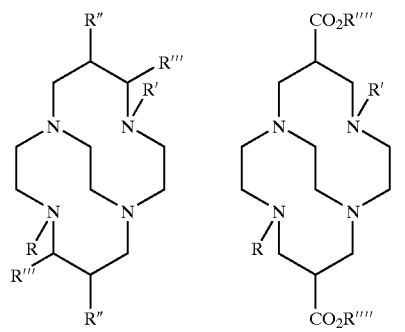
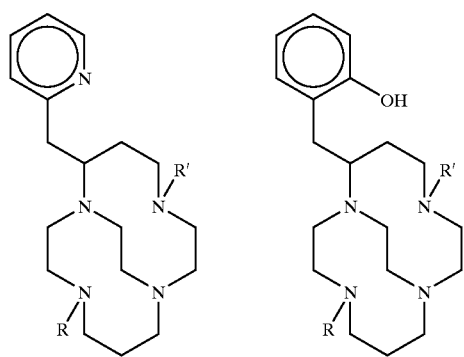

In the above, the R, R', R'', R''' moieties can, for example, be methyl, ethyl or propyl. (Note that in the above formalism, the short straight strokes attached to certain N atoms are an alternate representation for a methyl group).

While the above illustrative structures involve tetra-aza derivatives (four donor nitrogen atoms), ligands and the corresponding complexes in accordance with the present invention can also be made, for example from any of the following:

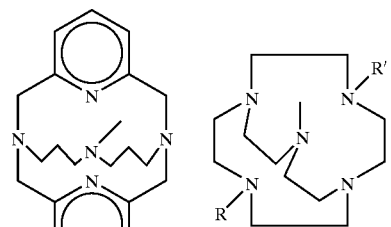
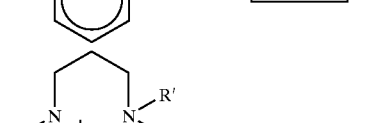
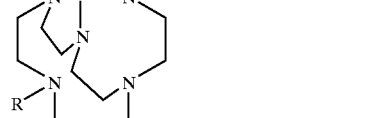
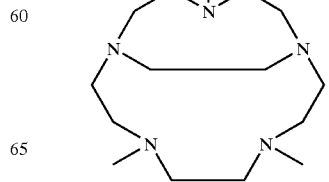
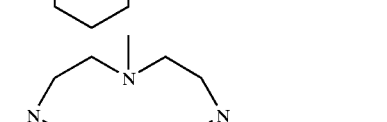
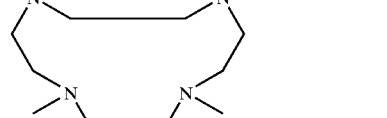

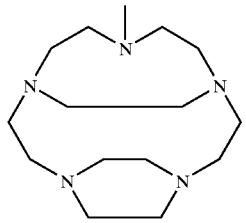

Moreover, using only a single organic macropolycycle, preferably a cross-bridged derivative of cyclam, a wide range of oxidation catalyst compounds of the invention may be prepared; numerous of these are believed to be novel chemical compounds. Preferred transition-metal catalysts of both cyclam-derived and non-cyclam-derived cross-bridged kinds are illustrated, but not limited, by the following:

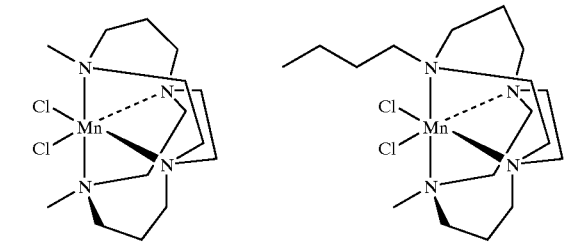

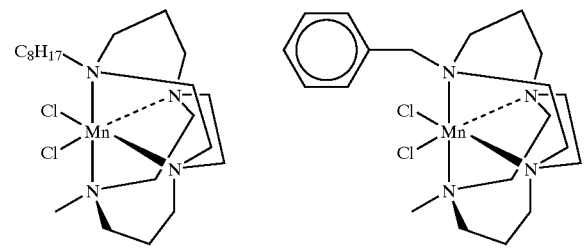

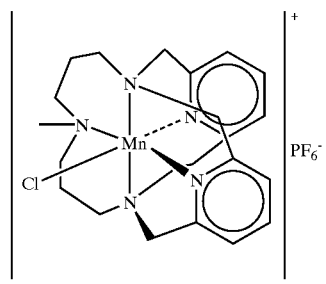

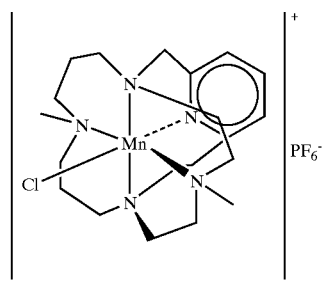

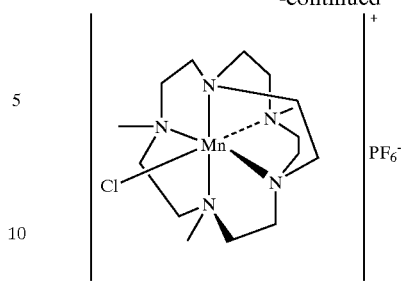

In other embodiments of the invention, transition-metal complexes, such as the Mn, Fe or Cr complexes, especially (II) and/or (III) oxidation state complexes, of the hereinabove-identified metals with any of the following ligands are also included:

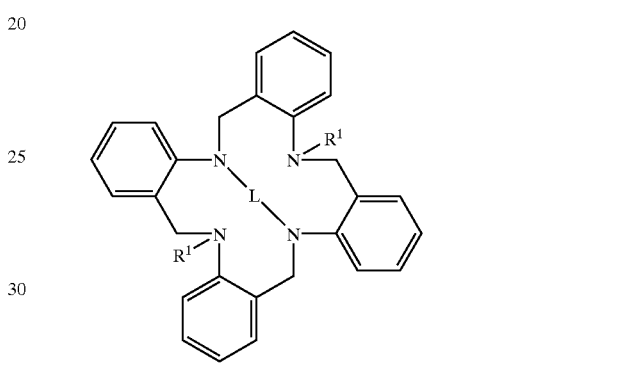

wherein $R^1$ is independently selected from H (preferably non-H) and linear or branched, substituted or unsubstituted $C_1$–$C_{20}$ alkyl, alkenyl or alkynyl and L is any of the linking moieties given herein, for example 1.10 or 1.11;

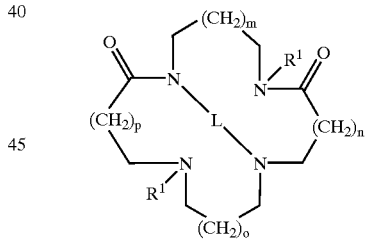

wherein $R^1$ is as defined supra; m,n,o and p can vary independently and are integers which can be zero or a positive integer and can vary independently while respecting the provision that the sum m+n+o+p is from 0 to 8 and L is any of the linking moieties defined herein;

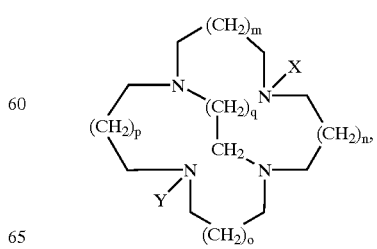

-continued

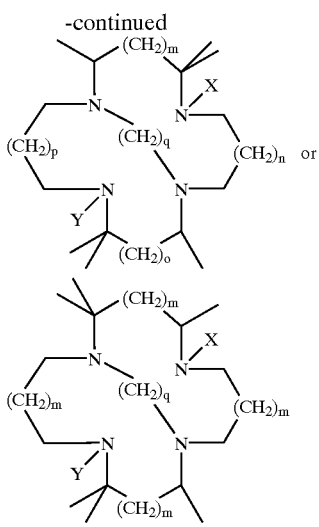

wherein X and Y can be any of the $R^1$ defined supra, m,n,o and p are as defined supra and q is an integer, preferably from 1 to 4; or, more generally,

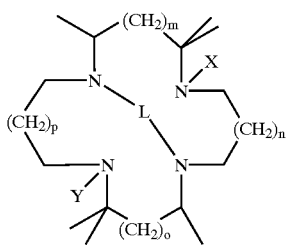

wherein L is any of the linking moieties herein, X and Y can be any of the $R^1$ defined supra, and m, n, o and p are as defined supra. Alternately, another useful ligand is:

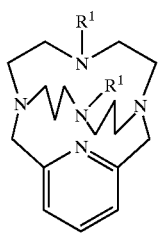

wherein $R^1$ is any of the $R^1$ moieties defined supra.

Pendant Moieties

Macropolycyclic rigid ligands and the corresponding transition-metal complexes and oxidation catalytic systems herein may also incorporate one or more pendant moieties, in addition to, or as a replacement for, $R^1$ moieties. Such pendant moieties are nonlimitingly illustrated by any of the following:

—$(CH_2)_n$—$CH_3$—$(CH_2)_n$—$C(O)NH_2$

—$(CH_2)_n$—CN—$(CH_2)_n$—$C(O)OH$

—$(CH2)_n$—$C(O)NR_2$—$(CH_2)_n$—OH

—$(CH_2)_n$—$C(O)OR$

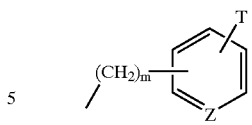

wherein R is, for example, a C1–C12 alkyl, more typically a C1–C4 alkyl, and Z and T are as defined in 1.11. Pendant moieties may be useful, for example, if it is desired to adjust the solubility of the catalyst in a particular solvent adjunct.

Alternately, complexes of any of the foregoing highly rigid, cross-bridged macropolycyclic ligands with any of the metals indicated are equally within the invention.

Preferred are catalysts wherein the transition metal is selected from manganese and iron, and most preferably manganese. Also preferred are catalysts wherein the molar ratio of transition metal to macropolycyclic ligand in the oxidation catalyst is 1:1, and more preferably wherein the catalyst comprises only one metal per oxidation catalyst complex. Further preferred transition-metal oxidation catalysts are monometallic, mononuclear complexes. The term "monometallic, mononuclear complex" is used herein in referring to an essential transition-metal oxidation catalyst compound to identify and distinguish a preferred class of compounds containing only one metal atom per mole of compound and only one metal atom per mole of cross-bridged macropolycyclic ligand.

Preferred transition-metal oxidation catalysts also include those wherein at least four of the donor atoms in the macropolycyclic rigid ligand, preferably at least four nitrogen donor atoms, two of which form an apical bond angle with the same transition metal of 180±50° and two of which form at least one equatorial bond angle of 90±20°. Such catalysts preferably have four or five nitrogen donor atoms in total and also have coordination geometry selected from distorted octahedral (including trigonal antiprismatic and general tetragonal distortion) and distorted trigonal prismatic, and preferably wherein further the cross-bridged macropolycyclic ligand is in the folded conformation (as described, for example, in Hancock and Martell, Chem. Rev., 1989, 89, at page 1894). A folded conformation of a cross-bridged macropolycyclic ligand in a transition-metal complex is further illustrated below:

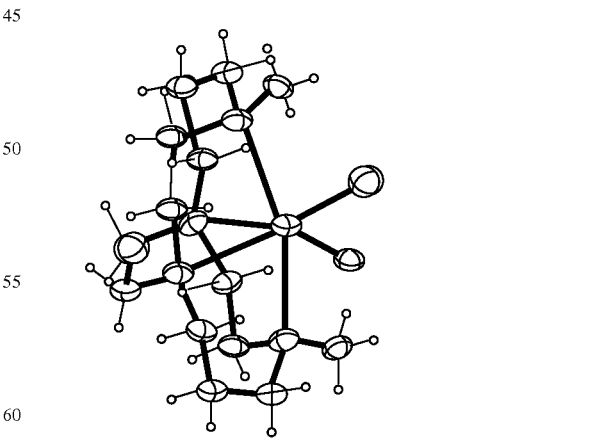

This catalyst is the complex of Example 1 hereinafter. The center atom is Mn; the two ligands to the right are chloride; and a Bcyclam ligand occupies the left side of the distorted octahedral structure. The complex contains an angle N—Mn—N of 158° incorporating the two mutually trans-donor atoms in "axial" positions; the corresponding angle N—Mn—N for the nitrogen donor atoms in plane with the two chloride ligands is 83.2°.

Stated alternately, the preferred synthetic, laundry, cleaning, papermaking, or effluent-treating catalytic systems herein contain transition-metal complexes of a macropolycyclic ligand in which there is a major energetic preference of the ligand for a folded, as distinct from an "open" and/or "planar" and or "flat" conformation. For comparison, a disfavored conformation is, for example, either of the trans- structures shown in Hancock and Martell, *Chemical Reviews*, (1989), 89 at page 1894 (see FIG. 18), incorporated by reference.

In light of the foregoing coordination description, the present invention includes oxidation catalytic systems comprising a transition-metal oxidation catalyst, especially based on Mn(II) or Mn(III) or correspondingly, Fe(II) or Fe(III) or Cr(II) or Cr(III), wherein two of the donor atoms in the macropolycyclic rigid ligand, preferably two nitrogen donor atoms, occupy mutually trans- positions of the coordination geometry, and at least two of the donor atoms in the macropolycyclic rigid ligand, preferably at least two nitrogen donor atoms, occupy cis- equatorial positions of the coordination geometry, including particularly the cases in which there is substantial distortion as illustrated hereinabove.

The present catalytic systems can, furthermore, include transition metal oxidation catalysts in which the number of asymmetric sites can vary widely; thus both S— and R— absolute conformations can be included for any stereochemically active site. Other types of isomerism, such as geometric isomerism, are also included. The transition-metal oxidation catalyst can further include mixtures of geometric or stereoisomers.

Purification of Catalyst

In general, the state of purity of the transition-metal oxidation catalyst can vary, provided that any impurities, such as byproducts of the synthesis, free ligand(s), unreacted transition-metal salt precursors, colloidal organic or inorganic particles, and the like, are not present in amounts which substantially decrease the utility of the transition-metal oxidation catalyst. It has been discovered that preferred embodiments of the present invention include those in which the transition-metal oxidation catalyst is purified by any suitable means, such that it does not excessively consume available oxygen (AvO). Excessive AvO consumption is defined as including any instance of exponential decrease in AvO levels of bleaching, oxidizing or catalyzing solutions with time at 20–40 deg. C. Preferred transition-metal oxidation catalysts herein, whether purified or not, when placed into dilute aqueous buffered alkaline solution at a pH of about 9 (carbonate/bicarbonate buffer) at temperatures of about 40 deg. C., have a relatively steady decrease in AvO levels with time; in preferred cases, this rate of decrease is linear or approximately linear. In the preferred embodiments, there is a rate of AvO consumption at 40 deg C. given by a slope of a graph of % AvO vs. time (in sec.) (hereinafter "AvO slope") of from about −0.0050 to about −0.0500, more preferably −0.0100 to about −0.0200. Thus, a preferred Mn(II) oxidation catalyst in accordance with the invention has an AvO slope of from about −0.0140 to about −0.0182; in contrast, a somewhat less preferred transition metal oxidation catalyst has an AvO slope of −0.0286.

Preferred methods for determining AvO consumption in aqueous solutions of transition metal oxidation catalysts herein include the well-known iodometric method or its variants, such as methods commonly applied for hydrogen peroxide. See, for example, Organic Peroxides, Vol. 2., D. Swern (Ed.,), Wiley-Interscience, New York, 1971, for example the table at p. 585 and references therein including P. D. Bartlett and R. Altscul, J. Amer. Chem. Soc., 67, 812 (1945) and W. E. Cass, J. Amer. Chem. Soc., 68, 1976 (1946). Accelerators such as ammonium molybdate can be used. The general procedure used herein is to prepare an aqueous solution of catalyst and hydrogen peroxide in a mild alkaline buffer, for example carbonate/bicarbonate at pH 9, and to monitor the consumption of hydrogen peroxide by periodic removal of aliquots of the solution which are "stopped" from further loss of hydrogen peroxide by acidification using glacial acetic acid, preferably with chilling (ice). These aliquots can then be analyzed by reaction with potassium iodide, optionally but sometimes preferably using ammonium molybdate (especially low-impurity molybdate, see for example U.S. Pat. No. 4,596,701) to accelerate complete reaction, followed by back-titratation using sodium thiosulfate. Other variations of analytical procedure can be used, such as thermometric procedures, potential buffer methods (Ishibashi et al., Anal. Chim. Acta (1992), 261(1–2), 405–10) or photometric procedures for determination of hydrogen peroxide (EP 485,000 A2, May 13, 1992). Variations of methods permitting fractional determinations, for example of peracetic acid and hydrogen peroxide, in presence or absence of the instant transition-metal oxidation catalysts are also useful; see, for example JP 92–303215, Oct. 16, 1992.

In another embodiment of the present invention, there are encompassed laundry and cleaning compositions incorporating transition-metal oxidation catalysts which have been purified to the extent of having a differential AvO loss reduction, relative to the untreated catalyst, of at least about 10% (units here are dimensionless since they represent the ratio of the AvO slope of the treated transition-metal oxidation catalyst over the AvO slope for the untreated transition metal oxidation catalyst—effectively a ratio of AvO's). In other terms, the AvO slope is improved by purification so as to bring it into the above-identified preferred ranges.

In yet another embodiment of the instant invention, two processes have been identified which are particularly effective in improving the suitability of transition-metal oxidation catalysts, as synthesized, for incorporation into laundry and cleaning products or for other useful oxidation catalysis applications.

One such process is any process having a step of treating the transition-metal oxidation catalyst, as prepared, by extracting the transition-metal oxidation catalyst, in solid form, with an aromatic hydrocarbon solvent; suitable solvents are oxidation-stable under conditions of use and include benzene and toluene, preferably toluene. Surprisingly, toluene extraction can measurably improve the AvO slope (see disclosure hereinabove).

Another process which can be used to improve the AvO slope of the transition metal oxidation catalyst is to filter a solution thereof using any suitable filtration means for removing small or colloidal particles. Such means include the use of fine-pore filters; centrifugation; or coagulation of the colloidal solids.

In more detail, a full procedure for purifying a transition-metal oxidation catalyst herein can include:

(a) dissolving the transition-metal oxidation catalyst, as prepared, in hot acetonitrile:

(b) filtering the resulting solution hot, e.g., at about 70 deg. C., through glass microfibers (for example glass microfiber filter paper available from Whatman);

(c) if desired, filtering the solution of the first filtration through a 0.2 micron membrane (for example, a 0.2 micron filter commercially available from Millipore) or centrifuging whereby colloidal particles are removed;

(d) evaporating the solution of the second filtration to dryness;

(e) washing the solids of step (d) with toluene, for example five times using toluene in an amount which is double the volume of the oxidation catalyst solids;

(f) drying the product of step (e).

Another procedure which can be used, in any convenient combination with aromatic solvent washes and/or removal of fine particles is recrystallization. Recrystallization, for example of Mn(II) Bcyclam chloride transition-metal oxidation catalyst, can be done from hot acetonitrile. Recrystallization can have its disadvantages, for example it may on occasion be more costly.

Catalytic Systems and Methods for Synthetic Oxidation Reactions

Methods and catalytic systems for oxidizing alkenes to epoxides by treating the alkene with a transition-metal complex are known, for example from U.S. Pat. No. 5,428,180 and U.S. Pat. No. 5,077,394. Epoxidations of olefins can also be carried out according to the method of Collman, J. P.; Kodadek, T. J.; Raybuck, S. A.; and Meunier, B., *Proc. Natl. Acad. Sci. U.S.A* (1983), 80, 7039, and which publication is incorporated herein by reference in its entirety. In the present invention, catalytic systems and methods require the presence of the transition-metal oxidation catalysts described herein to effect such oxidative processes.

The catalytic systems for use herein suitably comprise a transition-metal oxidation catalyst as described herein, a primary oxidation agent or primary oxidant, for example monopersulfate or peracetic acid or their salts, and a solvent. A wide range of protic and aprotic solvents can be used, covering a range of dielectric constants. The catalytic systems include solutions comprising at least about 0.00001%, more preferably at least about 0.0001% of transition-metal catalyst, from about 0.0001% to about 10%, by weight of primary oxidation agent, and at least about 5%, more typically at least about 50% of solvent. The amount of substrate (the compound to be oxidized) can vary in a wide range, in terms of proportion by weight to the catalytic system. A suitable range of composition is from 1:10,000 to about 10,000:1 of catalytic system to substrate by weight, more typically from about 1:1,000 to about 1:1.

Similarly, other oxidation reactions for synthetic chemical manufacturing processes such as oxidation of sulfides to sulfones are carried out according to the present invention utilizing catalytic systems containing oxidation agent, transition-metal catalysts, and proportions of the materials as described herein. Again, it is preferred that such processes use catalytic systems which are solutions of these agents.

Catalytic systems and Methods for Pulp Oxidation

The application of oxidizing agents in a sequence of delignifying and bleaching treatment stages of unbleached chemical paper pulp processes are known, for example U.S. Pat. No. 5,431,781. The present invention catalytic systems and methods further require the presence of the transition-metal oxidation catalysts described herein to effect such oxidative processes.

All types of wood used for the production of chemical pulps are suitable for use in the process of the present invention. In particular, this includes those used for kraft pulps, namely the coniferous woods such as, for example, the species of pines and firs and the deciduous woods such as, for example, yellow pine, beech, oak, eucalyptus and hornbeam.

Catalytic systems useful in pulp and paper treatment can, in general, have a range of composition similar to that described supra for organic synthetic purposes. The substrate in this instance is paper or paper-derived materials having an oxidizable component, such as lignin.

In more detail, transition-metal catalysts herein can be useful in a somewhat similar manner to the substituted porphyrin metal complexes of Dolphin (U.S. Pat. No. 5,077,394), though there can be additional advantages, for example improved flexibility in the control of water-solubility of catalyst as compared with certain porphyrin systems. Thus transition-metal complexes identified herein may be used in the form of catalyst systems including (a) the transition-metal catalyst, (b) primary oxidant, for example peracetate, persulfate or peroxide, and (c) solvent such as water though nonaqueous, especially polar aprotic solvents such as dimethylformamide, acetonitrile, dimethylsulfoxide, alcohols e.g., methanol, ethanol, chlorinated solvents such as dichloromethane, chloroform or the like or combinations of water and such organic solvents having a wide range in dielectric constant may be used, together providing catalytic systems for oxidation applicable to a variety of processes, for example those in which prior art optionally substituted phenyl porphyrins have been indicated as useful. The transition-metal catalysts which are the more water soluble are particularly useful in those processes in which water solubility is desired or required. Such processes include, by way of illustration, the oxidation of alkanes (including cycloalkanes), the oxidation of alkenes (including cycloalkenes), the oxidative conversion of lignin model compounds which are converted by the lignin modifying and degrading fungal enzymes also known as ligninases, the use in the modification or degradation of lignin, and the use in the treating of wood in various forms such as wood chips or pulp to assist in or effect pulping or bleaching.

Particular pulping-related processes of interest for the use of the water soluble transition-metal complexes, for example the Mn(II) Bcyclam complexes, for assisting in or effecting a modification or degradation of lignin, include processes of making and oxidatively treating the well-known mechanical pulps such as thermomechanical pulps and kraft pulps so as to effect bleaching.

The invention also provides transition-metal complexes having reduced water-solubility, such as those in which the macrocycle ligand carries one or more long-chain alkyl pendant substituents, and these may also be used in various commercial applications such as solvent pulping, for example the known organosolv pulping process. Other uses include the decomposition of organic contaminants in waste streams such as the chlorinated organic compounds in EI effluent from the kraft pulp chlorine bleaching process.

Of particular interest is the use of the present transition-metal catalysts, including the Fe, Mn (preferred for environmental reasons) and even Ni types as catalysts in the catalytic oxidation of alkanes (including cycloalkanes) for the hydroxylation of the same (or ultimate keto formation) and in the catalytic oxidation of alkenes (including cycloalkenes) to form epoxides (epoxidation). Such hydroxylations and epoxidation are well-known reactions which are commonly carried out in an organic solvent which is redox-inert under the operating conditions, but water containing systems may also be used; hence both the water soluble and water insoluble transition-metal complexes may be used in such processes.

In general, the present transition-metal oxidant catalytic systems may be used over a wide range of reaction temperatures including high temperatures up to 150 deg. C. or even higher, and over a wide range of pH's which may extend from about 1 to 14, more suitably from pH 2 to pH 12; nonetheless, it is particularly desirable to use the catalysts at ambient or near-ambient temperatures where energy economy is desired, and to use mild pH's, which are desirably safe for material handling. The present catalyst systems have the advantage of being useful under such conditions.

The present invention includes use of the identified transition-metal oxidation catalyst systems in the oxidative delignification of wood-pulp. U.S. Pat. No. 5,552,019, for example, describes such delignification using polyoxometallates. The present catalyst systems, typically comprising (a) the transition-metal catalyst; (b) a primary oxidant such as sodium hypochlorite or, more preferably, potassium monopersulfate triple salt, the latter sold commercially as OXONE by Du Pont and (c) pH-adjusting adjuncts can be used, especially at pH in the range from about 7.5 to about 9.5, under mild temperature conditions for delignification purposes.

The present invention has numerous alternate embodiments and ramifications. For example, in the laundry detergents and laundry detergent additives field, the invention includes all manner of bleach-containing or bleach additive compositions, including for example, fully-formulated heavy-duty granular detergents containing sodium perborate or sodium percarbonate and/or a preformed peracid derivative such as OXONE as primary oxidant, the transition-metal catalyst of the invention, a bleach activator such as tetraacetylethylenediamine or a similar compound, with or without nonanoyloxybenzenesulfonate sodium salt, and the like.

Other suitable composition forms include laundry bleach additive powders, granular or tablet-form automatic dishwashing detergents, scouring powders and bathroom cleaners. In the solid-form compositions, the catalytic system may lack solvent (water)—this is added by the user along with the substrate (a soiled surface) which is to be cleaned (or contains soil to be oxidized).

Other desirable embodiments of the instant invention include dentifrice or denture cleaning compositions. Suitable compositions to which the transition-metal complexes herein can be added include the dentifrice compositions containing stabilized sodium percarbonate, see for example U.S. Pat. No. 5,424,060 and the denture cleaners of U.S. Pat. No. 5,476,607 which are derived from a mixture containing a pregranulated compressed mixture of anhydrous perborate, perborate monohydrate and lubricant, monopersulfate, non-granulated perborate monohydrate, proteolytic enzyme and sequestering agent, though enzyme-free compositions are also very effective. Optionally, excipients, builders, colors, flavors, and surfactants can be added to such compositions, these being adjuncts characteristic of the intended use. RE32,771 describes another denture cleaning composition to which the instant transition-metal catalysts may profitably be added. Thus, by simple admixture of, for example, about 0.00001% to about 0.1% of the present transition-metal catalyst, a cleaning composition is secured that is particularly suited for compaction into tablet form; this composition also comprises a phosphate salt, an improved perborate salt mixture wherein the improvement comprises a combination of anhydrous perborate and monohydrate perborate in the amount of about 50% to about 70% by weight of the total cleansing composition, wherein the combination includes at least 20% by weight of the total cleansing composition of anhydrous perborate, said combination having a portion present in a compacted granulated mixture with from about 0.01% to about 0.70% by weight of said combination of a polymeric fluorocarbon, and a chelating or sequestering agent present in amounts greater than about 10% by weight up to about 50% by weight of the total composition, said cleansing composition being capable of cleansing stained surfaces and the like with a soaking time of five minutes or less when dissolved in aqueous solution and producing a marked improvement in clarity of solution upon disintegration and cleaning efficacy over the prior art. Of course, the denture cleaning composition need not extend to the sophistication of such compositions: adjuncts not essential to the provision of catalytic oxidation such as the fluorinated polymer can be omitted if desired.

In another non-limiting illustration, the present transition-metal catalyst can be added to an effervescent denture-cleaning composition comprising monoperphthalate, for example the magnesium salt thereof, and/or to the composition of U.S. Pat. No. 4,490,269 incorporated herein by reference. Preferred denture cleansing compositions include those having tablet form, wherein the tablet composition is characterized by active oxygen levels in the range from about 100 to about 200 mg/tablet; and compositions characterized by fragrance retention levels greater than about 50% throughout a period of six hours or greater. See U.S. Pat. No. 5,486,304 incorporated by reference for more detail in connection especially with fragrance retention.

The advantages and benefits of the instant invention include cleaning compositions which have superior bleaching compared to compositions not having the selected transition-metal oxidation catalyst. The superiority in bleaching is obtained using very low levels of transition-metal oxidation catalyst. The invention includes embodiments which are especially suited for fabric washing, having a low tendency to damage fabrics in repeated washings. However, numerous other benefits can be secured; for example, compositions an be relatively more aggressive, as needed, for example, in tough cleaning of durable hard surfaces, such as the interiors of ovens, or kitchen surfaces having difficult-to-remove films of soil. The compositions can be used both in "pre-treat" modes, for example to loosen dirt in kitchens or bathrooms; or in a "mainwash" mode, for example in fully-formulated heavy-duty laundry detergent granules. Moreover, in addition to the bleaching and/or soil-removing advantages, other advantages of the instant compositions include their efficacy in improving the sanitary condition of surfaces ranging from laundered textiles to kitchen counter-tops and bathroom tiles. Without intending to be limited by theory, it is believed that the compositions can help control or kill a wide variety of micro-organisms, including bacteria, viruses, sub-viral particles and molds; as well as to destroy objectionable non-living proteins and/or peptides such as certain toxins.

The transition-metal oxidation catalysts useful herein may be synthesized by any convenient route. However, specific synthesis methods are nonlimitingly illustrated in detail as follows, including a synthetic method according to the present invention wherein the catalyst is prepared under strictly oxygen and hydroxyl-free conditions by use of bis(pyridine) manganese (II) salts (e.g., chloride salt) to coordinate the manganese into the macropolycyclic rigid ligand [see, for example, Example 1, Method I, and Example 7].

EXAMPLE 1

Synthesis of [Mn(Bcyclam)Cl₂]

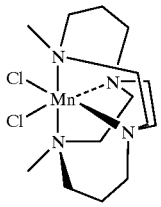

(a) Method I.

"Bcyclam" (5,12-dimethyl-1,5,8,12-tetraaza-bicyclo[6.6.2]hexadecane) is prepared by a synthesis method described by G. R. Weisman, et al., *J.Amer.Chem.Soc.*, (1990), 112 8604. Bcyclam (1.00 g., 3.93 mmol) is dissolved in dry $CH_3CN$ (35 mL, distilled from $CaH_2$). The solution is then evacuated at 15 mm until the $CH_3CN$ begins to boil. The flask is then brought to atmospheric pressure with Ar. This degassing procedure is repeated 4 times. Mn(pyridine)₂Cl₂ (1.12 g., 3.93 mmol), synthesized according to the literature procedure of H. T. Witteveen et al., *J. Inorg. Nucl. Chem.*, (1974), 36, 1535, is added under Ar. The cloudy reaction solution slowly begins to darken. After stirring overnight at room temperature, the reaction solution becomes dark brown with suspended fine particulates. The reaction solution is filtered with a $0.2\mu$ filter. The filtrate is a light tan color. This filtrate is evaporated to dryness using a rotoevaporator. After drying overnight at 0.05 mm at room temperature, 1.35 g. off-white solid product is collected, 90% yield. Elemental Analysis: % Mn, 14.45; % C, 44.22; % H, 7.95; theoretical for [Mn(Bcyclam)Cl₂], $MnC_{14}H_{30}N_4Cl_2$, MW=380.26. Found: % Mn, 14.98; % C, 44.48; % H, 7.86; Ion Spray Mass Spectroscopy shows one major peak at 354 mu corresponding to [Mn(Bcyclam)(formate)]⁺.

(b) Method II.

Freshly distilled Bcyclam (25.00 g., 0.0984 mol), which is prepared by the same method as above, is dissolved in dry $CH_3CN$ (900 mL, distilled from $CaH_2$). The solution is then evacuated at 15 mm until the $CH_3CN$ begins to boil. The flask is then brought to atmospheric pressure with Ar. This degassing procedure is repeated 4 times. $MnCl_2$ (11.25 g., 0.0894 mol) is added under Ar. The cloudy reaction solution immediately darkens. After stirring 4 hrs. under reflux, the reaction solution becomes dark brown with suspended fine particulates. The reaction solution is filtered through a $0.2\mu$ filter under dry conditions. The filtrate is a light tan color. This filtrate is evaporated to dryness using a rotoevaporator. The resulting tan solid is dried overnight at 0.05 mm at room temperature. The solid is suspended in toluene (100 mL) and heated to reflux. The toluene is decanted off and the procedure is repeated with another 100 mL of toluene. The balance of the toluene is removed using a rotoevaporator. After drying overnight at 0.05 mm at room temperature, 31.75 g. of a light blue solid product is collected, 93.5% yield. Elemental Analysis: % Mn, 14.45; % C, 44.22; % H, 7.95; % N, 14.73; % Cl, 18.65; theoretical for [Mn(Bcyclam)Cl₂], $MnC_{14}H_{30}N_4Cl_2$, MW=380.26. Found: % Mn, 14.69; % C, 44.69; % H, 7.99; % N, 14.78; % Cl, 18.90 (Karl Fischer Water, 0.68%). Ion Spray Mass Spectroscopy shows one major peak at 354 mu corresponding to [Mn(Bcyclam)(formate)]⁺.

EXAMPLE 2

Synthesis of [Mn(C₄-Bcyclam)Cl₂] where C₄-Bcyclam=5-n-butyl-12-methyl-1,5,8,12-tetraazabicyclo[6.6.21]hexadecane

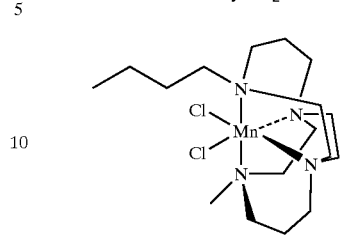

(a) C₄-Bcyclam Synthesis

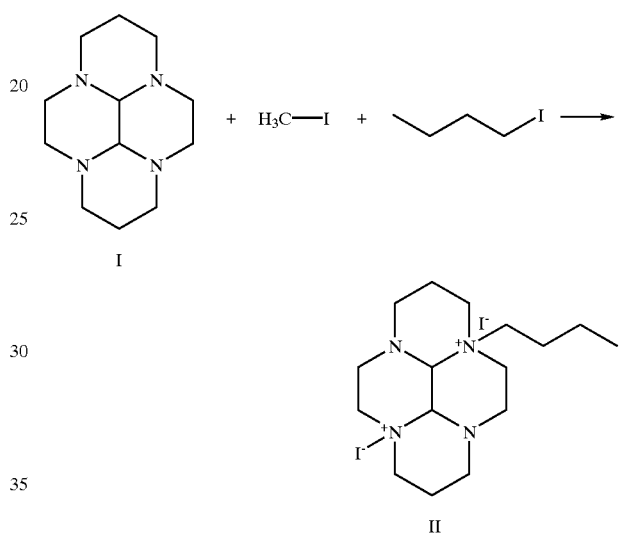

Tetracyclic adduct I is prepared by the literature method of H. Yamamoto and K. Maruoka, *J. Amer. Chem. Soc.*, (1981), 103, 4194. I (3.00 g., 13.5 mmol) is dissolved in dry $CH_3CN$ (50 mL, distilled from $CaH_2$). 1-Iodobutane (24.84 g., 135 mmol) is added to the stirred solution under Ar. The solution is stirred at room temperature for 5 days. 4-Iodobutane (12.42 g., 67.5 mmol) is added and the solution is stirred an additional 5 days at RT. Under these conditions, I is fully mono-alkylated with 1-iodobutane as shown by ¹³C-NMR. Methyl iodide (26.5 g, 187 mmol) is added and the solution is stirred at room temperature for an additional 5 days. The reaction is filtered using Whatman #4 paper and vacuum filtration. A white solid, II, is collected (6.05 g., 82%). ¹³C NMR (CDCl₃) 16.3, 21.3, 21.6, 22.5, 25.8, 49.2, 49.4, 50.1, 51.4, 52.6, 53.9, 54.1, 62.3, 63.5, 67.9, 79.1, 79.2 ppm. Electro spray Mass Spec. (MH⁺/2, 147).

II (6.00 g., 11.0 mmol) is dissolved in 95% ethanol (500 mL). Sodium borohydride (11.0 g., 290 mmol) is added and the reaction turns milky white. The reaction is stirred under Ar for three days. Hydrochloric acid (100 mL, concentrated) is slowly dripped into the reaction mixture over 1 hour. The reaction mixture is evaporated to dryness using a rotoevaporator. The white residue is dissolved in sodium hydroxide (500 mL, 1.00N). This solution is extracted with toluene (2×150 mL). The toluene layers are combined and dried with sodium sulfate. After removal of the sodium sulfate using filtration, the toluene is evaporated to dryness using a rotoevaporator. The resulting oil is dried at room temperature under high vacuum (0.05 mm) overnight. A colorless oil results 2.95 g., 90%. This oil (2.10 g.) is distilled using a short path distillation apparatus (still head temperature 115 C. at 0.05 mm). Yield: 2.00 g. $^{13}$C NMR (CDCl$_3$) 14.0, 20.6, 27.2, 27.7, 30.5, 32.5, 51.2, 51.4, 54.1, 54.7, 55.1, 55.8, 56.1, 56.5, 57.9, 58.0, 59.9 ppm. Mass Spec. (MH$^+$, 297).

(b) [Mn C$_4$-Bcyclam)Cl$_2$] Synthesis

C$_4$-Bcyclam (2.00 g., 6.76 mmol) is slurried in dry CH$_3$CN (75 mL, distilled from CaH$_2$). The solution is then evacuated at 15 mm until the CH$_3$CN begins to boil. The flask is then brought to atmospheric pressure with Ar. This degassing procedure is repeated 4 times. MnCl$_2$ (0.81 g., 6.43 mmol) is added under Ar. The tan, cloudy reaction solution immediately darkens. After stirring 4 hrs. under reflux, the reaction solution becomes dark brown with suspended fine particulates. The reaction solution is filtered through a 0.2µ membrane filter under dry conditions. The filtrate is a light tan color. This filtrate is evaporated to dryness using a rotoevaporator. The resulting white solid is suspended in toluene (50 mL) and heated to reflux. The toluene is decanted off and the procedure is repeated with another 100 mL of toluene. The balance of the toluene is removed using a rotoevaporator. After drying overnight at 0.05 mm, RT, 2.4 g. a light blue solid results, 88% yield. Ion Spray Mass Spectroscopy shows one major peak at 396 mu corresponding to [Mn(C$_4$-Bcyclam)(formate)]$^+$.

EXAMPLE 3

Synthesis of [Mn(Bz-Bcyclam)Cl$_2$] where Bz-Bcyclam=5-benzyl-12-methyl-1,5,8,1 2-tetraaza-bicyclo[6.6.2]hexadecane

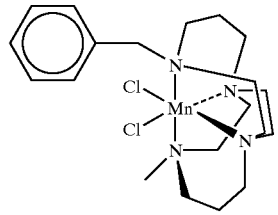

(a) Bz-Bcyclam Synthesis

This ligand is synthesized similarly to the C$_4$-Bcyclam synthesis described above in Example 2(a) except that benzyl bromide is used in place of the 1-iodobutane. $^{13}$C NMR (CDCl$_3$) 27.6, 28.4, 43.0, 52.1, 52.2, 54.4, 55.6, 56.4, 56.5, 56.9, 57.3, 57.8, 60.2, 60.3, 126.7, 128.0, 129.1, 141.0 ppm. Mass Spec. (MH$^+$, 331).

(b) [Mn(Bz-Bcyclam)Cl$_2$] Synthesis

This complex is made similarly to the [Mn(C$_4$-Bcyclam) Cl$_2$] synthesis described above in Example 2(b) except that Bz-Bcyclam is used in place of the C$_4$-Bcyclam.

Ion Spray Mass Spectroscopy shows one major peak at 430 mu corresponding to [Mn(Bz-Bcyclam)(formate)]$^+$.

EXAMPLE 4

Synthesis of [Mn(C$_8$-Bcyclam)Cl$_2$] where C$_8$-Bcyclam=5-n-octyl-12-methyl-1,5,8,12-tetraaza-bicyclo[6.6.21]hexadecane

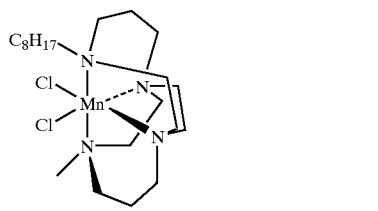

(a) C$_8$-Bcyclam Synthesis:

This ligand is synthesized similarly to the C$_4$-Bcyclam synthesis described above in Example 2(a) except that 1-iodooctane is used in place of the 1-iodobutane.

Mass Spec. (MH$^+$, 353).

(b) [Mn(C$_8$-Bcyclam)Cl$_2$] Synthesis

This complex is made similarly to the [Mn(C$_4$-Bcyclam) Cl$_2$] synthesis described above in Example 2(b) except that C$_8$-Bcyclam is used in place of the C$_4$-Bcyclam.

Ion Spray Mass Spectroscopy shows one major peak at 452 mu corresponding to [Mn(B$_8$-Bcyclam)(formate)]$^+$.

EXAMPLE 5

Synthesis of [Mn(H$_2$-Bcyclam)Cl$_2$] where H$_2$-Bcyclam=1,5,8,12-tetraaza-bicyclo[6.6.21]hexadecane The H$_2$-Bcyclam is synthesized similarly to the C$_4$-Bcyclam synthesis described above except that benzyl bromide is used in place of the 1-iodobutane and the methyl iodide. The benzyl groups are removed by catalytic hydrogenation. Thus, the resulting 5,12-dibenzyl-1,5,8,12-tetraaza-bicyclo[6.6.2]hexadecane and 10% Pd on charcoal is dissolved in 85% acetic acid. This solution is stirred 3 days at room temperature under 1 atm. of hydrogen gas. The solution is filtered though a 0.2 micron filter under vacuum. After evaporation of solvent using a rotary evaporator, the product is obtained as a colorless oil. Yield: 90$^+$%.

The Mn complex is made similarly to the [Mn(Bcyclam) Cl$_2$] synthesis described in Example 1(b) except that the that H$_2$-Bcyclam is used in place of the Bcyclam.

Elemental Analysis: % C, 40.92; % H, 7.44; % N, 15.91; theoretical for [Mn(H$_2$-Bcyclam)Cl$_2$], MnC$_{12}$H$_{26}$N$_4$Cl$_2$, MW=352.2. Found: % C, 41.00; % H, 7.60; % N, 15.80. FAB+ Mass Spectroscopy shows one major peak at 317 mu corresponding to [Mn(H$_2$-Bcyclam)Cl]$^+$ and another minor peak at 352 mu corresponding to [Mn(H$_2$-Bcyclam)Cl$_2$]$^+$.

EXAMPLE 6

Synthesis of [Fe(H$_2$-Bcyclam)Cl$_2$] where H$_2$-Bcyclam=1,5,8,12-tetraaza-bicyclo[6.6.2]hexadecane

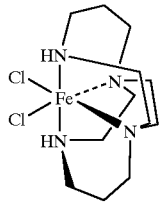

The Fe complex is made similarly to the [Mn(H$_2$-Bcyclam)Cl$_2$] synthesis described in Example 5 except that the that anhydrous FeCl$_2$ is used in place of the MnCl$_2$.

Elemental Analysis: % C, 40.82; % H, 7.42; % N, 15.87; theoretical for [Fe(H$_2$-Bcyclam)Cl$_2$], FeC$_{12}$H$_{26}$N$_4$Cl$_2$, MW=353.1. Found: % C, 39.29; % H, 7.49; % N, 15.00. FAB+ Mass Spectroscopy shows one major peak at 318 mu corresponding to [Fe(H$_2$-Bcyclam)Cl]$^+$ and another minor peak at 353 mu corresponding to [Fe(H$_2$-Bcyclam)Cl$_2$]$^+$.

EXAMPLE 7

Synthesis of:

Chloro-20-methyl-1,9,20,24,25-pentaaza-tetracyclo[7.7.7.1$^{3,7}$.1$^{11,15}$.]pentacosa-3,5,7(24),11,13,15(25)-hexaene manganese(II) hexafluorophosphate ,7(b); Trifluoromethanesulfono-20-methyl-1,9,20,24,25-pentaaza tetracyclo[7.7.7.1$^{3,7}$.1$^{11,15}$.]pentacosa-3,5,7(24),11,13,15(25)-hexaene manganese(II) trifluoromethanesulfonate, 7(c) and Thiocyanato-20-methyl-1,9,20,24,25-pentaaza-tetracyclo[7.7.7.1$^{3,7}$.1$^{11,15}$.]pentacosa-3,5,7(24),11,13,15(25)-hexaene iron(II) thiocyanate, 7(d)

(a) Synthesis of the Ligand 20-methyl-1,9,20,24,25-pentaaza-tetracyclo[7.7.7.1$^{3,7}$.1$^{11,15}$.]pentacosa-3,5,7(24), 11,13,15(25)-hexaene The ligand 7-methyl-3,7, 11, 17-tetraazabicyclo[11.3.1$^{17}$] heptadeca-1(17), 13,15-triene is synthesized by the literature procedure of K. P. Balakrishnan et al., *J. Chem. Soc., Dalton Trans.,* 1990, 2965.

7-methyl-3,7,11,17-tetraazabicyclo[11.3.1$^{17}$]heptadeca-1(17), 13,15-triene (1.49 g, 6 mmol) and O,O'-bis(methanesulfonate)-2,6-pyridine dimethanol (1.77 g, 6 mmol) are separately dissolved in acetonitrile (60 ml). They are then added via a syringe pump (at a rate of 1.2 ml/hour) to a suspension of anhydrous sodium carbonate (53 g, 0.5 mol) in acetonitrile (1380 ml). The temperature of the reaction is maintained at 65° C. throughout the total reaction of 60 hours.

After cooling, the solvent is removed under reduced pressure and the residue is dissolved in sodium hydroxide solution (200 ml, 4M). The product is then extracted with benzene (6 times 100 ml) and the combined organic extracts are dried over anhydrous sodium sulfate. After filtration the solvent is removed under reduced pressure. The product is then dissolved in an acetonitrile/triethylamine mixture (95:5) and is passed through a column of neutral alumina (2.5×12 cm). Removal of the solvent yields a white solid (0.93 g, 44%).

This product may be further purified by recrystallization from an ethanol/diethylether mixture combined with cooling at 0° C. overnight to yield a white crystalline solid. Anal. Calcd. for C$_{21}$H$_{29}$N$_5$: C, 71.75; H, 8.32; N, 19.93. Found: C, 71.41; H, 8.00; N, 20.00. A mass spectrum displays the expected molecular ion peak [for C$_{21}$H$_{30}$N$_5$]$^+$ at m/z=352. The $^1$H NMR(400 MHz, in CD$_3$CN) spectrum exhibits peaks at δ=1.81 (m,4H); 2.19 (s, 3H); 2.56 (t, 4H); 3.52 (t,4H); 3.68 (AB, 4H), 6.53 (d, 4H) and 7.07 (t, 2H). The $^{13}$C NMR(75.6 MHz, in CD$_3$CN) spectrum shows eight peaks at δ=24.05, 58.52, 60.95, 62.94, 121.5, 137.44 and 159.33 ppm.

All metal complexation reactions are performed in an inert atmosphere glovebox using distilled and degassed solvents.

(b) Complexation of the Ligand L$_1$ with bis(pyridine) manganese (II) chloride

Bis(pyridine)manganese (II) chloride is synthesized according to the literature procedure of H. T. Witteveen et al., *J. Inorg. Nucl. Chem.,* 1974, 36, 1535.

The ligand L$_1$ (1.24 g, 3.5 mmol), triethylamine(0.35 g, 3.5 mmol) and sodium hexafluorophosphate (0.588 g, 3.5 mmol) are dissolved in pyridine (12 ml). To this is added bis(pyridine)manganese (II) chloride and the reaction is stirred overnight. The reaction is then filtered to remove a white solid. This solid is washed with acetonitrile until the washings are no longer colored and then the combined organic filtrates are evaporated under reduced pressure. The residue is dissolved in the minimum amount of acetonitrile and allowed to evaporate overnight to produce bright red crystals. Yield: 0.8 g (39%). Anal. Calcd. for C$_{21}$H$_{31}$N$_5$Mn$_1$Cl$_1$P$_1$F$_6$: C, 43.00; H, 4.99 and N, 11.95. Found: C, 42.88; H, 4.80 and N 11.86. A mass spectrum displays the expected molecular ion peak [for C$_{21}$H$_{31}$N$_5$Mn$_1$Cl$_1$] at m/z=441. The electronic spectrum of a dilute solution in water exhibits two absorption bands at 260 and 414 nm (ε=1.47×10$^3$ and 773 M$^{-1}$ cm$^{-1}$ respectively). The IR spectrum (KBr) of the complex shows a band at 1600 cm$^{-1}$ (pyridine), and strong bands at 840 and 558 cm$^{-1}$ (PF$_6^-$).

(c) Complexation of the Ligand with manganese (II) trifluoromethanesulfonate

Manganese (II) trifluoromethanesulfonate is prepared by the literature procedure of Bryan and Dabrowiak, Inorg. Chem., 1975, 14, 297.

Manganese (II) trifluoromethanesulfonate (0.883 g, 2.5 mmol) is dissolved in acetonitrile (5 ml). This is added to a solution of the ligand L$_1$(0.878 g, 2.5 mmol) and triethylamine (0.25 g, 2.5 mmol) in acetonitrile (5 ml). This is then heated for two hours before filtering and then after cooling removal of the solvent under reduced pressure. The residue is dissolved in a minimum amount of acetonitrile and left to evaporate slowly to yield orange crystals. Yield 1.06 g (60%). Anal. Calc. for Mn$_1$C$_{23}$H$_{29}$N$_5$S$_2$F$_6$O$_6$: C, 39.20; H, 4.15 and N, 9.95. Found: C, 38.83; H, 4.35 and N, 10.10. The mass spectrum displays the expected peak for [Mn$_1$C$_{22}$H$_{29}$N$_5$S$_1$F$_3$O$_3$]$^+$ at m/z=555. The electronic spectrum of a dilute solution in water exhibits two absorption bands at 260 and 412 nm (ε=9733 and 607 M$^{-1}$ cm$^{-1}$ respectively). The IR spectrum (KBr) of the complex shows a band at 1600 cm$^{-1}$ (pyridine) and 1260, 1160 and 1030 cm$^{-1}$(CF$_3$SO$_3$).

(d) Complexation of the Ligand with iron (II) trifluoromethanesulfonate

Iron (II) trifluoromethanesulfonate is prepared in situ by the literature procedure Tait and Busch, *Inorg. Synth.,* 1978, XVIII, 7.

The ligand (0.833 g, 2.5 mmol) and triethylamine (0.505 g, 5 mmol) are dissolved in acetonitrile (5 ml). To this is added a solution of hexakis(acetonitrile) iron (II) trifluoromethanesulfonate (1.5 g, 2.5 mmol) in acetonitrile (5 ml) to yield a dark red solution. Sodium thiocyanate (0.406 g, 5 mmol) is then added and the reaction stirred for a further hour. The solvent is then removed under reduced pressure and the resulting solid is recrystallized from methanol to produce red microcrystals. Yield: 0.65 g (50%). Anal. Calc. for $Fe_1C_{23}H_{29}N_7S_2$:C, 52.76; H, 5.59 and N, 18.74. Found: C 52.96; H, 5.53; N, 18.55. A mass spectrum displays the expected molecular ion peak [for $Fe_1C_{22}H_{29}N_6S_1$]$^+$ at m/z= 465. The $^1$H NMR (300 MHz, $CD_3CN$) δ=1.70(AB,2H), 2.0 (AB,2H), 2.24 (s,3H), 2.39 (m,2H), 2.70 (m,4H), 3.68 (m,4H), 3.95 (m,4H), 4.2 (AB,2H), 7.09 (d,2H), 7.19 (d,2H), 7.52 (t,1H), 7.61 (d,1H). The IR spectrum (KBr) of the spectrum shows peaks at 1608 cm$^{-1}$ (pyridine) and strong peaks at 2099 and 2037 cm$^{-1}$ (SCN$^-$). Example 8[Mn (Bcyclam)Cl$_2$] is used in a catalytic system including the transition metal complex, water as solvent, and t-butyl peroxide as primary oxidant, to catalyze the oxidation of a lignin model compound. See U.S. Pat. No. 5,077,394, Example 9, incorporated by reference, for details. The Mn complex replaces the iron porphyrin complex of '394.

EXAMPLE 8

[Mn(Bcyclam)Cl$_2$] is used in a catalytic system including the transition metal complex, dimethylformamide as solvent, and peracetate as primary oxidant, to catalyze the oxidation of lignin. See U.S. Pat. No. 5,077,394, Example 10, incorporated by reference, for details. The Mn complex replaces the iron porphyrin complex of this patent. In more detail, 250 micrograms of the Kraft softwood lignin Indulin AT (Westvaco Corporation, Charleston Heights, S.C.) is dissolved in 2 ml DMF. Peracetic acid is used as the primary oxidant at a final concentration of 1.84 micromolar. The Mn complex is used at a final concentration of 500 micromolar. The reaction mixture is stirred at room temperature for 24 hours and the resulting products are analyzed by gel permeation chromatography; any convenient column and solvent arrangement may suffice, though a TSK 4000 column with 1:1 chloroform:dioxane (Phenomenex, Rancho Palos Verdes, Calif.) may be useful. Absorbance is monitored at a suitable wavelength, for example 280 nm, and a distinct shift of the peaked area to the right indicates that a degradation of lignin has occurred.

EXAMPLE 9

[Mn(Bcyclam)Cl$_2$] is used in a catalytic system including the transition metal complex, water, and a range of different primary oxidants, to catalyze the oxidation of veratryl alcohol to veratrylaldehyde. See U.S. Pat. No. 5,077,394, Example 11, incorporated by reference, for details. The Mn complex replaces the manganese porphyrin complex of this patent. The oxidants include hydrogen peroxide, sodium hypochlorite, t-butylhydroperoxide, cumylhydroperoxide, potassium iodate and iodosylbenzene and the experiments are carried out over a range of pH of from 1 to 13 and with a variety of oxidant concentrations. The product is veratrylaldehyde. Yields tend to vary with pH and time, with evidence of product formation being obtained under a variety of conditions including slightly acid (e.g., pH 6.5) to mildly alkaline (e.g., pH 8.5–9). The catalyst effects an improvement over non-catalyzed reaction.

EXAMPLE 10

[Mn(Bcyclam)Cl$_2$] is used in a catalytic system including the transition metal complex, solvent, and primary oxidant, to epoxidize cylohexene. See U.S. Pat. No. 5,077,394, Example 13, incorporated by reference, for one possible procedure. The Mn complex replaces the complexes used in this patent.

EXAMPLE 11

[Mn(Bcyclam)Cl$_2$] is used in a catalytic system including the transition metal complex, water as solvent, and hydrogen peroxide/peracetic acid buffered in sodium carbonate/bicarbonate at pH of about 9, to oxidize a blue dye, suitably Chicago Sky Blue 6B (Aldrich), to a colorless product. The reaction can be monitored by ultraviolet spectroscopy.

Oxidation Agents:

Oxidation agents (sometimes termed "oxidants") useful in the present invention can be any of the oxidizing agents known for oxidative synthetic reaction chemistry, pulp oxidation and bleaching, laundry, hard surface cleaning, automatic dishwashing or denture cleaning purposes. Oxygen bleaches or mixtures thereof are preferred, though other oxidants, such as oxygen, an enzymatic hydrogen peroxide producing system, or hypohalites, such as chlorine oxidants like hypochlorite, may also be used. Oxygen-based oxidants deliver "available oxygen" (AvO) or "active oxygen" which is typically measurable by standard methods such as iodide/thiosulfate and/or ceric sulfate titration. See the well-known work by Swern, or Kirk Othmer's Encyclopedia of Chemical Technology under "Bleaching Agents". When the oxidant is a peroxygen compound, it contains —O—O— linkages with one O in each such linkage being "active". AvO content of such an oxidant compound, usually expressed as a percent, is equal to 100* the number of active oxygen atoms* (16/ molecular weight of the oxygen bleach compound). Preferably, an oxygen bleach will be used herein, since this benefits most directly from combination with the catalyst. The mode of combination can vary. For example, the catalyst and oxidant can be incorporated into a single product formula, or can be used in various combinations of "pretreatment product" such as "stain sticks", "main wash product" and even "post-wash product" such as fabric conditioners or dryer-added sheets. The oxidant herein can have any physical form compatible with the intended application; more particularly, liquid-form and solid-form oxidants as well as adjuncts, promoters or activators are included. Liquids can be included in solid detergents, for example by adsorption onto an inert support; and solids can be included in liquid detergents, for example by use of compatible suspending agents. Common oxidants of the peroxygen type include hydrogen peroxide, inorganic peroxohydrates, organic peroxohydrates and the organic peroxyacids, including hydrophilic and hydrophobic mono- or di- peroxyacids. These can be peroxycarboxylic acids, peroxyimidic acids, amidoperoxycarboxylic acids, or their salts including the calcium, magnesium, or mixed-cation salts. Peracids of various kinds can be used both in free form and as precursors known as "bleach activators" or "bleach promoters" which, when combined with a source of hydrogen peroxide, perhydrolyze to release the corresponding peracid. Also useful herein as oxidants are the inorganic peroxides such as $Na_2O_2$, superoxides such as $KO_2$, organic hydroperoxides such as cumene hydroperoxide and t-butyl hydroperoxide, and the inorganic peroxoacids and their salts such as the peroxosulfuric acid salts, especially the potassium salts of peroxodisulfuric acid and, more preferably, of peroxomonosulfuric acid including the commercial triple-salt form sold as OXONE by Dupont and also any equivalent commercially available forms such as CUROX from Akzo or CAROAT from Degussa. Certain organic peroxides, such as dibenzoyl peroxide, may be useful, especially as additives rather than as primary oxygen bleach.

Mixed oxidants are generally useful, as are mixtures of any oxidants with the known bleach activators, organic catalysts, enzymatic catalysts and mixtures thereof; moreover such mixtures may further include brighteners, photobleaches and dye transfer inhibitors of types well-known in the art.

Preferred oxidants include the peroxohydrates, sometimes known as peroxyhydrates or peroxohydrates. These are organic or, more commonly, inorganic salts capable of releasing hydrogen peroxide rather readily. They include types in which hydrogen peroxide is present as a true crystal hydrate, and types in which hydrogen peroxide is incorporated covalently and is released chemically, for example by hydrolysis. Typically, peroxohydrates deliver hydrogen peroxide readily enough that it can be extracted in measurable amounts into the ether phase of an ether/water mixture. Peroxohydrates are characterized in that they fail to give the Riesenfeld reaction, in contrast to certain other oxidant types described hereinafter. Peroxohydrates are the most common examples of "hydrogen peroxide source" materials and include the perborates, percarbonates, perphosphates, and persilicates. Other materials which serve to produce or release hydrogen peroxide are, of course, useful. Mixtures of two or more peroxohydrates can be used, for example when it is desired to exploit differential solubility. Suitable peroxohydrates include sodium carbonate peroxyhydrate and equivalent commercial "percarbonate" oxidants, and any of the so-called sodium perborate hydrates, the "tetrahydrate" and "monohydrate" being preferred; though sodium pyrophosphate peroxyhydrate can be used. Many such peroxohydrates are available in processed forms with coatings, such as of silicate and/or borate and/or waxy materials and/or surfactants, or have particle geometries, such as compact spheres, which improve storage stability. By way of organic peroxohydrates, urea peroxyhydrate can also be useful herein.

Percarbonate oxidant includes, for example, dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Percarbonates and perborates are widely available in commerce, for example from FMC, Solvay and Tokai Denka.

Organic percarboxylic acids useful herein as the oxidants include magnesium monoperoxyphthalate hexahydrate, available from Interox, m-chloro perbenzoic acid and its salts, 4-nonylamino-4-oxoperoxybutyric acid and diperoxydodecanedioic acid and their salts. Such bleaches are disclosed in U.S. Pat. No. 4,483,781, U.S. Patent Application Ser. No. 740,446, Burns et al, filed Jun. 3, 1985, EP-A 133,354, published Feb. 20, 1985, and U.S. Pat. No. 4,412,934. Highly preferred oxidants also include 6-nonylamino-6-oxoperoxycaproic acid (NAPAA) as described in U.S. Pat. No. 4,634,551 and include those having formula HO—O—C(O)—R—Y wherein R is an alkylene or substituted alkylene group containing from 1 to about 22 carbon atoms or a phenylene or substituted phenylene group, and Y is hydrogen, halogen, alkyl, aryl or —C(O)—OH or —C(O)—O—OH.

Organic percarboxylic acids usable herein include those containing one, two or more peroxy groups and can be aliphatic or aromatic. When the organic percarboxylic acid is aliphatic, the unsubstituted acid suitably has the linear formula: HO—O—C(O)—(CH$_2$)$_n$—Y where Y can be, for example, H, CH$_3$, CH$_2$Cl, COOH, or C(O)OOH; and n is an integer from 1 to 20. Branched analogs are also acceptable. When the organic percarboxylic acid is aromatic, the unsubstituted acid suitably has formula: HO—O—C(O)—C$_6$H$_4$—Y wherein Y is hydrogen, alkyl, alkyhalogen, halogen, or —COOH or —C(O)OOH.

Monoperoxycarboxylic acids useful as oxidant herein are further illustrated by alkyl percarboxylic acids and aryl percarboxylic acids such as peroxybenzoic acid and ring-substituted peroxybenzoic acids, e.g., peroxy-alpha-naphthoic acid; aliphatic, substituted aliphatic and arylalkyl monoperoxy acids such as peroxylauric acid, peroxystearic acid, and N,N-phthaloylaminoperoxycaproic acid (PAP); and 6-octylamino-6-oxo-peroxyhexanoic acid. Monoperoxycarboxylic acids can be hydrophilic, such as peracetic acid, or can be relatively hydrophobic. The hydrophobic types include those containing a chain of six or more carbon atoms, preferred hydrophobic types having a linear aliphatic C8–C14 chain optionally substituted by one or more ether oxygen atoms and/or one or more aromatic moieties positioned such that the peracid is an aliphatic peracid. More generally, such optional substitution by ether oxygen atoms and/or aromatic moieties can be applied to any of the peracids or bleach activators herein. Branched-chain peracid types and aromatic peracids having one or more C3–C16 linear or branched long-chain substituents can also be useful. The peracids can be used in the acid form or as any suitable salt with a bleach-stable cation. Very useful herein are the organic percarboxylic acids of formula:

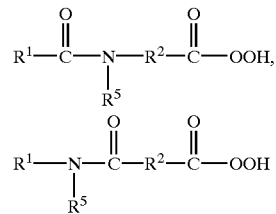

or mixtures thereof wherein R$^1$ is alkyl, aryl, or alkaryl containing from about 1 to about 14 carbon atoms, R$^2$ is alkylene, arylene or alkarylene containing from about 1 to about 14 carbon atoms, and R$^5$ is H or alkyl, aryl, or alkaryl containing from about 1 to about 10 carbon atoms. When these peracids have a sum of carbon atoms in R$^1$ and R$^2$ together of about 6 or higher, preferably from about 8 to about 14, they are particularly suitable as hydrophobic peracids for bleaching a variety of relatively hydrophobic or "lipophilic" stains, including so-called "dingy" types. Calcium, magnesium, or substituted ammonium salts may also be useful.

Other useful peracids and bleach activators herein are in the family of imidoperacids and imido bleach activators. These include phthaloylimidoperoxycaproic acid and related arylimido-substituted and acyloxynitrogen derivatives. For listings of such compounds, preparations and their incorporation into laundry compositions including both granules and liquids, See U.S. Pat. No. 5,487,818; U.S. Pat. No. 5,470,988, U.S. Pat. No. 5,466,825; U.S. Pat. No. 5,419,846; U.S. Pat. No. 5,415,796; U.S. Pat. No. 5,391,324; U.S. Pat. No. 5,328,634; U.S. Pat. No. 5,310,934; U.S. Pat. No. 5,279,757; U.S. Pat. No. 5,246,620; U.S. Pat. No. 5,245,075; U.S. Pat. No. 5,294,362; U.S. Pat. No. 5,423,998; U.S. Pat. No. 5,208,340; U.S. Pat. No. 5,132,431 and U.S. Pat. No. 5,087,385.

Useful diperoxyacids include, for example, 1,12-diperoxydodecanedioic acid (DPDA); 1,9-diperoxyazelaic acid; diperoxybrassilic acid; diperoxysebasic acid and diperoxyisophthalic acid; 2-decyldiperoxybutane-1,4-dioic acid; and 4,4'-sulphonylbisperoxybenzoic acid. Owing to structures in which two relatively hydrophilic groups are disposed at the ends of the molecule, diperoxyacids have sometimes been classified separately from the hydrophilic and hydrophobic monoperacids, for example as "hydrotropic": Some of the diperacids are hydrophobic in a quite literal sense, especially when they have a long-chain moiety separating the peroxyacid moieties.

More generally, the terms "hydrophilic" and "hydrophobic" used herein in connection with any of the oxidants, especially the peracids, and in connection with bleach activators, are in the first instance based on whether a given oxidant effectively performs bleaching of fugitive dyes in solution thereby preventing fabric greying and discoloration and/or removes more hydrophilic stains such as tea, wine and grape juice—in this case it is termed "hydrophilic". When the oxidant or bleach activator has a significant stain removal, whiteness-improving or cleaning effect on dingy, greasy, carotenoid, or other hydrophobic soils, it is termed "hydrophobic". The terms are applicable also when referring to peracids or bleach activators used in combination with a hydrogen peroxide source. The current commercial benchmarks for hydrophilic performance of oxidant systems are: TAED or peracetic acid, for benchmarking hydrophilic bleaching. NOBS or NAPAA are the corresponding benchmarks for hydrophobic bleaching. The terms "hydrophilic", "hydrophobic" and "hydrotropic" with reference to oxidants including peracids and here extended to bleach activator have also been used somewhat more narrowly in the literature. See especially Kirk Othmer's Encyclopedia of Chemical Technology, Vol. 4., pages 284–285. This reference provides a chromatographic retention time and critical micelle concentration-based set of criteria, and is useful to identify and/or characterize preferred sub-classes of hydrophobic, hydrophilic and hydrotropic oxidants and bleach activators that can be used in the present invention.

Bleach Activators

Bleach activators useful herein include amides, imides, esters and anhydrides. Commonly at least one substituted or unsubstituted acyl moiety is present, covalently connected to a leaving group as in the structure R—C(O)-L. In one preferred mode of use, bleach activators are combined with a source of hydrogen peroxide, such as the perborates or percarbonates, in a single product. Conveniently, the single product leads to in situ production in aqueous solution (i.e., during the washing process) of the percarboxylic acid corresponding to the bleach activator. The product itself can be hydrous, for example a powder, provided that water is controlled in amount and mobility such that storage stability is acceptable. Alternately, the product can be an anhydrous solid or liquid. In another mode, the bleach activator or oxygen bleach is incorporated in a pretreatment product, such as a stain stick; soiled, pretreated substrates can then be exposed to further treatments, for example of a hydrogen peroxide source. With respect to the above bleach activator structure RC(O)L, the atom in the leaving group connecting to the peracid-forming acyl moiety R(C)O— is most typically O or N. Bleach activators can have non-charged, positively or negatively charged peracid-forming moieties and/or noncharged, positively or negatively charged leaving groups. One or more peracid-forming moieties or leaving-groups can be present. See, for example, U.S. Pat. No. 5,595,967, U.S. Pat. No. 5,561,235, U.S. Pat. No. 5,560,862 or the bis-(peroxy-carbonic) system of U.S. Pat. No. 5,534,179. Bleach activators can be substituted with electron-donating or electron-releasing moieties either in the leaving-group or in the peracid-forming moiety or moieties, changing their reactivity and making them more or less suited to particular pH or wash conditions. For example, electron-withdrawing groups such as $NO_2$ improve the efficacy of bleach activators intended for use in mild-pH (e.g., from about 7.5–to about 9.5) wash conditions.

Cationic bleach activators include quaternary carbamate-, quaternary carbonate-, quaternaryester- and quaternary amide-types, delivering a range of cationic peroxyimidic, peroxycarbonic or peroxycarboxylic acids to the wash. An analogous but non-cationic palette of bleach activators is available when quaternary derivatives are not desired. In more detail, cationic activators include quaternary ammonium-substituted activators of WO 96-06915, U.S. Pat. Nos. 4,751,015 and 4,397,757, EP-A-284292, EP-A-331,229 and EP-A-03520 including 2-(N,N,N-trimethyl ammonium) ethyl-4-sulphophenyl carbonate-(SPCC); N-octyl,N,N-dimethyl-N 10-carbophenoxy decyl ammonium chloride-(ODC); 3-(N,N,N-trimethyl ammonium) propyl sodium-4-sulphophenyl carboxylate; and N,N,N-trimethyl ammonium toluyloxy benzene sulfonate. Also useful are cationic nitriles as disclosed in EP-A-303,520 and in European Patent Specification 458,396 and 464,880. Other nitrile types have electron-withdrawing substituents as described in U.S. Pat. No. 5,591,378; examples including 3,5-dimethoxybenzonitrile and 3,5-dinitrobenzonitrile.

Other bleach activator disclosures include GB 836,988; 864,798; 907,356; 1,003,310 and 1,519,351; German Patent 3,337,921; EP-A-0185522; EP-A-0174132; EP-A-0120591; U.S. Pat. Nos. 1,246,339; 3,332,882; 4,128,494; 4,412,934 and 4,675,393, and the phenol sulfonate ester of alkanoyl aminoacids disclosed in U.S. Pat. No. 5,523,434. Suitable bleach activators include any acetylated diamine types, whether hydrophilic or hydrophobic in character.

Of the above classes of bleach precursors, preferred classes include the esters, including acyl phenol sulfonates, acyl alkyl phenol sulfonates or acyl oxybenzenesulfonates (OBS leaving-group); the acyl-amides; and the quaternary ammonium substituted peroxyacid precursors including the cationic nitriles.

Preferred bleach activators include N,N,N'N'-tetraacetyl ethylene diamine (TAED) or any of its close relatives including the triacetyl or other unsymmetrical derivatives. TAED and the acetylated carbohydrates such as glucose pentaacetate and tetraacetyl xylose are preferred hydrophilic bleach activators. Depending on the application, acetyl triethyl citrate, a liquid, also has some utility, as does phenyl benzoate.

Preferred hydrophobic bleach activators include sodium nonanoyloxybenzene sulfonate (NOBS or SNOBS), substituted amide types described in detail hereinafter, such as activators related to NAPAA, and activators related to certain imidoperacid bleaches, for example as described in U.S. Pat. No. 5,061,807, issued Oct. 29, 1991 and assigned to Hoechst Aktiengesellschaft of Frankfurt, Germany. Japanese Laid-Open Patent Application (Kokai) No. 4–28799 for example describes a bleaching agent and a bleaching detergent composition comprising an organic peracid precursor described by a general formula and illustrated by com pounds which may be summarized more particularly as conforming to the formula:

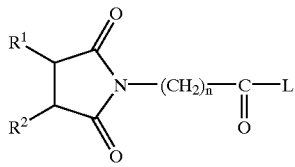

wherein L is sodium p-phenolsulfonate, $R^1$ is $CH_3$ or $C_{12}H_{25}$ and $R^2$ is H. Analogs of these compounds having any of the leaving-groups identified herein and/or having R1 being linear or branched C6–C16 are also useful.

Another group of peracids and bleach activators herein are those derivable from acyclic imidoperoxycarboxylic acids and salts thereof of the formula:

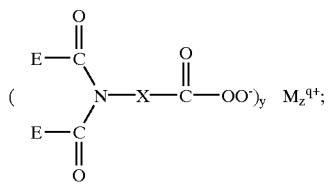

cyclic imidoperoxycarboxylic acids and salts thereof of the formula

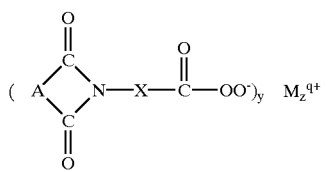

and (iii) mixtures of said compounds, (i) and (ii);
wherein M is selected from hydrogen and bleach-compatible cations having charge q; and y and z are integers such that said compound is electrically neutral; E, A and X comprise hydrocarbyl groups; and said terminal hydrocarbyl groups are contained within E and A. The structure of the corresponding bleach activators is obtained by deleting the peroxy moiety and the metal and replacing it with a leaving-group L, which can be any of the leaving-group moieties defined elsewhere herein. In preferred embodiments, there are encompassed detergent compositions wherein, in any of said compounds, X is linear $C_3$–$C_8$ alkyl; A is selected from:

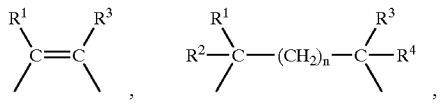

wherein n is from 0 to about 4, and

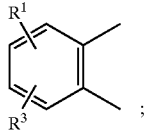

wherein $R^1$ and E are said terminal hydrocarbyl groups, $R^2$, $R^3$ and $R^4$ are independently selected from H, $C_1$–$C_3$ saturated alkyl, and $C_1$–$C_3$ unsaturated alkyl; and wherein said terminal hydrocarbyl groups are alkyl groups comprising at least six carbon atoms, more typically linear or branched alkyl having from about 8 to about 16 carbon atoms.

Other suitable bleach activators include sodium-4-benzoyloxy benzene sulfonate (SBOBS); sodium-1-methyl-2-benzoyloxy benzene-4-sulphonate; sodium-4-methyl-3-benzoyloxy benzoate (SPCC); trimethyl ammonium toluyloxy-benzene sulfonate; or sodium 3,5,5-trimethyl hexanoyloxybenzene sulfonate (STHOBS).

Bleach activators may be used in an amount of up to 20%, preferably from 0.1–10% by weight, of the composition, though higher levels, 40% or more, are acceptable, for example in highly concentrated bleach additive product forms or forms intended for appliance automated dosing.

Highly preferred bleach activators useful herein are amide-substituted and have either of the formulae:

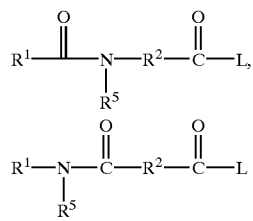

or mixtures thereof, wherein $R^1$ is alkyl, aryl, or alkaryl containing from about 1 to about 14 carbon atoms including both hydrophilic types (short $R^1$) and hydrophobic types ($R^1$ is especially from about 8 to about 12), $R^2$ is alkylene, arylene or alkarylene containing from about 1 to about 14 carbon atoms, $R^5$ is H, or an alkyl, aryl, or alkaryl containing from about 1 to about 10 carbon atoms, and L is a leaving group.

A leaving group as defined herein is any group that is displaced from the bleach activator as a consequence of attack by perhydroxide or equivalent reagent capable of liberating a more potent bleach from the reaction. Perhydrolysis is a term used to describe such reaction. Thus bleach activators perhydrolyze to liberate peracid. Leaving groups of bleach activators for relatively low-pH washing are suitably electron-withdrawing. Preferred leaving groups have slow rates of reassociation with the moiety from which they have been displaced. Leaving groups of bleach activators are preferably selected such that their removal and peracid formation are at rates consistent with the desired application, e.g., a wash cycle. In practice, a balance is struck such that leaving-groups are not appreciably liberated, and the corresponding activators do not appreciably hydrolyze or perhydrolyze, while stored in a bleaching composition. The pK of the conjugate acid of the leaving group is a measure of suitability, and is typically from about 4 to about 16, preferably from about 6 to about 12, more preferably from about 8 to about 11.

Preferred bleach activators include those of the formulae, for example the amide-substituted formulae, hereinabove, wherein $R^1$, $R^2$ and $R^5$ are as defined for the corresponding peroxyacid and L is selected from the group consisting of:

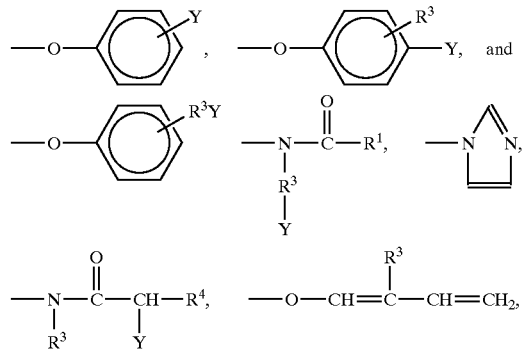

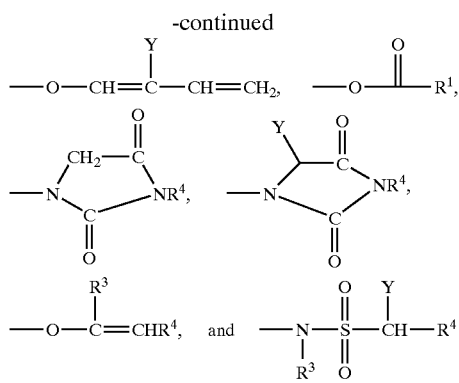

and mixtures thereof, wherein $R^1$ is a linear or branched alkyl, aryl, or alkaryl group containing from about 1 to about 14 carbon atoms, $R^3$ is an alkyl chain containing from 1 to about 8 carbon atoms, $R^4$ is H or $R^3$, and Y is H or a solubilizing group. These and other known leaving groups are, more generally, general suitable alternatives for introduction into any bleach activator herein. Preferred solubilizing groups include —$SO3^-M^+$, —$CO2^-M^+$, —$SO4^-M^+$, —$N^+(R)$ $4X^-$ and $O \leftarrow N(R^3)2$, more preferably —$SO3^-M^+$ and —$CO2^-M^+$ wherein $R^3$ is an alkyl chain containing from about 1 to about 4 carbon atoms, M is a bleach-stable cation and X is a bleach-stable anion, each of which is selected consistent with maintaining solubility of the activator. Under some circumstances, for example solid-form European heavy-duty granular detergents, any of the above bleach activators are preferably solids having crystalline character and melting-point above about 50 deg. C.; in these cases, branched alkyl groups are preferably not included in the oxygen bleach or bleach activator; in other formulation contexts, for example heavy-duty liquids with bleach or liquid bleach additives, low-melting or liquid bleach activators are preferred. Melting-point reduction can be favored by incorporating branched, rather than linear alkyl moieties into the oxygen bleach or precursor.

When solubilizing groups are added to the leaving group, the activator can have good water-solubility or dispersibility while still being capable of delivering a relatively hydrophobic peracid. Preferably, M is alkali metal, ammonium or substituted ammonium, more preferably Na or K, and X is halide, hydroxide, methylsulfate or acetate. Solubilizing groups can, more generally, be used in any bleach activator herein. Bleach activators of lower solubility, for example those with leaving group not having a solubilizing group, may need to be finely divided or dispersed in bleaching solutions for acceptable results.

Preferred bleach activators also include those of the above general formula wherein L is selected from the group consisting of:

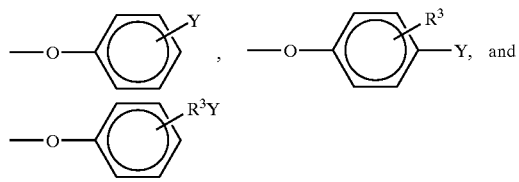

wherein $R^3$ is as defined above and Y is —$SO3^-M^+$ or —$CO2^-M^+$ wherein M is as defined above. Preferred examples of bleach activators of the above formulae include (6-octanamidocaproyl)oxybenzenesulfonate, (6-nonanamidocaproyl) oxybenzenesulfonate, (6-decanamidocaproyl)oxybenzenesulfonate, and mixtures thereof.

Other useful activators, disclosed in U.S. Pat. No. 4,966,723, are benzoxazin-type, such as a $C_6H_4$ ring to which is fused in the 1,2-positions a moiety—$C(O)OC(R^1)=N$—.

Depending on the activator and precise application, good bleaching results can be obtained from bleaching systems having with in-use pH of from about 6 to about 13, preferably from about 9.0 to about 10.5. Typically, for example, activators with electron-withdrawing moieties are used for near-neutral or sub-neutral pH ranges. Alkalis and buffering agents can be used to secure such pH.

Acyl lactam activators are very useful herein, especially the acyl caprolactams (see for example WO 94-28102 A) and acyl valerolactams (see U.S. Pat. No. 5,503,639) of the formulae:

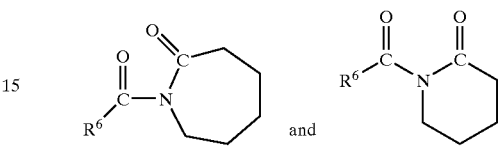

wherein $R^6$ is H, alkyl, aryl, alkoxyaryl, an alkaryl group containing from 1 to about 12 carbon atoms, or substituted phenyl containing from about 6 to about 18 carbons. See also U.S. Pat. No. 4,545,784 which discloses acyl caprolactams, including benzoyl caprolactam adsorbed into sodium perborate. In certain preferred embodiments of the invention, NOBS, lactam activators, imide activators or amide-functional activators, especially the more hydrophobic derivatives, are desirably combined with hydrophilic activators such as TAED, typically at weight ratios of hydrophobic activator: TAED in the range of 1:5 to 5:1, preferably about 1:1. Other suitable lactam activators are alpha-modified, see WO 96–22350 A1, Jul. 25, 1996. Lactam activators, especially the more hydrophobic types, are desirably used in combination with TAED, typically at weight ratios of amido-derived or caprolactam activators: TAED in the range of 1:5 to 5:1, preferably about 1:1. See also the bleach activators having cyclic amidine leaving-group disclosed in U.S. Pat. No. 5,552,556.

Nonlimiting examples of additional activators useful herein are to be found in U.S. Pat. No. 4,915,854, U.S. Pat. No. 4,412,934 and 4,634,551. The hydrophobic activator nonanoyloxybenzene sulfonate (NOBS) and the hydrophilic tetraacetyl ethylene diamine (TAED) activator are typical, and mixtures thereof can also be used.

The superior bleaching/cleaning action of the present compositions is also preferably achieved with safety to natural rubber machine parts, for example of certain european washing appliances (see WO 94-28104) and other natural rubber articles, including fabrics containing natural rubber and natural rubber elastic materials. Complexities of bleaching mechanisms are legion and are not completely understood.

Additional activators useful herein include those of U.S. Pat. No. 5,545,349. Examples include esters of an organic acid and ethylene glycol, diethylene glycol or glycerin, or the acid imide of an organic acid and ethylenediamine; wherein the organic acid is selected from methoxyacetic acid, 2-methoxypropionic acid, p-methoxybenzoic acid, ethoxyacetic acid, 2-ethoxypropionic acid, p-ethoxybenzoic acid, propoxyacetic acid, 2-propoxypropionic acid, p-propoxybenzoic acid, butoxyacetic acid, 2-butoxypropionic acid, p-butoxybenzoic acid, 2-methoxyethoxyacetic acid, 2-methoxy-1-methylethoxyacetic acid, 2-methoxy-2-methylethyacetic acid,2-ethoxyethoxyacetic acid, 2-(2-ethoxyethoxy) propionic acid, p-(2-ethoxyethoxy)benzoic acid, 2-ethoxy-1-methylethoxyacetic acid, 2-ethoxy-2-methylethoxyacetic acid, 2-propoxyethoxyacetic acid, 2-propoxy-1-methylethoxyaceticacid, 2-propoxy-2-methylethoxyacetic acid, 2-butoxyethoxyacetic acid, 2-butoxy-1-methylethoxyacetic acid, 2-butoxy-2-methylethoxyacetic acid, 2-(2-methoxyethoxy)ethoxyacetic acid, 2-(2-methoxy-1-methylethoxy)ethoxyacetic acid, 2-(2-methoxy-2-methylethoxy)ethoxyacetic acid and 2-(2-ethoxyethoxy) ethoxyacetic acid.

Enzymatic Sources of Hydrogen Peroxide

On a different track from the bleach activators illustrated hereinabove, another suitable hydrogen peroxide generating system is a combination of a $C_1$–$C_4$ alkanol oxidase and a $C_1$–$C_4$ alkanol, especially a combination of methanol oxidase (MOX) and ethanol. Such combinations are disclosed in WO 94/03003. Other enzymatic materials related to bleaching, such as peroxidases, haloperoxidases, oxidases, superoxide dismutases, catalases and their enhancers or, more commonly, inhibitors, may be used as optional ingredients in the instant compositions.

Oxygen Transfer Agents and Precursors

Also useful herein are any of the known organic bleach catalysts, oxygen transfer agents or precursors therefor. These include the compounds themselves and/or their precursors, for example any suitable ketone for production of dioxiranes and/or any of the hetero-atom containing analogs of dioxirane precursors or dioxiranes, such as sulfonimines $R^1R^2C\!\!=\!\!NSO_2R^3$, see EP 446 982 A, published 1991 and sulfonyloxaziridines, for example:

see EP 446,981 A, published 1991. Preferred examples of such materials include hydrophilic or hydrophobic ketones, used especially in conjunction with monoperoxysulfates to produce dioxiranes in situ, and/or the imines described in U.S. Pat. No. 5,576,282 and references described therein. Oxygen bleaches preferably used in conjunction with such oxygen transfer agents or precursors include percarboxylic acids and salts, percarbonic acids and salts, peroxymonosulfuric acid and salts, and mixtures thereof. See also U.S. Pat. No. 5,360,568; U.S. Pat. No. 5,360,569; and U.S. Pat. No. 5,370,826.

Catalytic System Combinations

While the combinations of ingredients used with the transition-metal bleach catalysts of the invention can be widely permuted, some particularly preferred combinations include:

(a) transition metal bleach catalyst+hydrogen peroxide source alone, e.g., sodium perborate or percarbonate;

(b) as (a) but with the further addition of a bleach activator selected from (i) hydrophilic bleach activators;

(ii) hydrophobic bleach activators and (iii) mixtures thereof;

(c) transition metal bleach catalyst+peracid alone, e.g., (i) hydrophilic peracid, e.g., peracetic acid;

(ii) hydrophobic peracid, e.g., NAPAA or peroxylauric acid;

(iii) inorganic peracid, e.g., peroxymonosulfuric acid K salts;

(d) use (a), (b) or (c) with the further addition of an oxygen transfer agent or precursor therefor; especially (c)+oxygen transfer agent. Any of (a)–(d) can be further combined with one or more polymeric dispersants, sequestrants, antioxidants, fluorescent whitening agents, photobleaches and/or dye transfer inhibitors. In such combinations, the transition metal bleach catalyst will preferably be at levels in a range suited to provide wash (in-use) concentrations of from about 0.1 to about 10 ppm (weight of catalyst); the other components being used at their known levels which may vary widely.

While there is currently no certain advantage, the transition metal catalysts of the invention can be used in combination with heretofore-disclosed transition metal bleach or dye transfer inhibition catalysts, such as the Mn or Fe complexes of triazacyclononanes, the Fe complexes of N,N-bis(pyridin-2-yl-methyl)-bis(pyridin-2-yl)methylamine (U.S. Pat. No. 5,580,485) and the like. For example, when the transition metal bleach catalyst is one disclosed to be particularly effective for solution bleaching and dye transfer inhibition, as is the case for example with certain transition metal complexes of porphyrins, it may be combined with one better suited for promoting interfacial bleaching of soiled substrates.

Laundry and Cleaning Compositions and Methods:

In general, a laundry or cleaning adjunct is any material required to transform a composition containing only transition-metal bleach catalyst into a composition useful for laundry or cleaning purposes. Adjuncts in general include detersive surfactants, builders, enzymes, and like materials having an independent cleaning function; and also stabilizers, diluents, structuring materials, agents having aesthetic effect such as colorants, pro-perfumes and perfumes. In preferred embodiments, laundry or cleaning adjuncts are readily recognizable to those of skill in the art as being characteristic of laundry or cleaning products, especially of laundry or cleaning products intended for direct use by a consumer in a domestic environment.

In a hard surface cleaning or fabric laundering operation which uses the present invention catalytic systems, the target substrate will typically be a fabric or surface stained with, for example, various food stains.

In the case of use in laundry or hard surface catalytic systems or methods, the catalytically effective amount of transition-metal oxidation catalyst is that sufficient to enhance the appearance of a soiled surface. In such cases, the appearance is typically improved in one or more of whiteness, brightness and de-staining; and a catalytically effective amount is one requiring less than a stoichiometric number of moles of catalyst when compared with the number of moles of primary oxidant, such as hydrogen peroxide or hydrophobic peracid, required to produce measurable effect. In addition to direct observation of the bulk surface being bleached or cleaned, catalytic bleaching effect can (where appropriate) be measured indirectly, such as by measurement of the kinetics or end-result of oxidizing a dye in solution.

By "effective amount" in a laundry or cleaning adjunct context is meant an amount of a material, such as a detergent adjunct, which is sufficient under whatever comparative or use conditions are employed, to provide the desired end-result benefit, for example in laundry and cleaning methods to improve the appearance of a soiled surface in one or more use cycles. A "use cycle" is, for example, one wash of a bundle of fabrics by a consumer. Appearance or visual effect can be measured by the consumer, by technical observers such as trained panelists, or by technical instrument means such as spectroscopy or image analysis.

Unless otherwise indicated, the detergent or detergent additive compositions may be formulated as granular or power-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tabletted, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

Catalytic systems herein as incorporated into detergents can include boron-free, phosphate-free, or chlorine-free embodiments.

Desirable adjuncts more generally include detersive surfactants, builders, enzymes, dispersant polymers, color speckles, silvercare, anti-tarnish and/or anti-corrosion agents, dyes, fillers, germicides, alkalinity sources, hydrotropes, anti-oxidants, enzyme stabilizing agents, perfumes, solubilizing agents, carriers, processing aids, pigments, and, for liquid formulations, solvents, as described in detail hereinafter.

Quite typically, laundry or cleaning compositions herein such as laundry detergents, laundry detergent additives, hard surface cleaners, automatic dishwashing detergents, synthetic and soap-based laundry bars, fabric softeners and fabric treatment liquids, solids and treatment articles of all kinds will require several adjuncts, though certain simply formulated products, such as bleach additives, may require only metal catalyst and a single supporting material such as a detergent builder or surfactant which helps to make the potent catalyst available to the consumer in a manageable dose.

Catalyst system compositions of the present invention useful for laundry or cleaning products comprise transition-metal bleach catalyst comprising a complex of a transition metal and a macropolycyclic rigid ligand as defined herein. The compositions also comprise at least one adjunct material, preferably comprising an oxygen bleaching agent such as a source of hydrogen peroxide. More preferably, the adjunct component includes both an oxygen bleaching agent and at least one other adjunct material selected from non-bleaching adjuncts suited for laundry detergents or cleaning products. Non-bleaching adjuncts as defined herein are adjuncts useful in detergents and cleaning products which neither bleach on their own, nor are recognized as adjuncts used in cleaning primarily as promoters of bleaching such as is the case with bleach activators, organic bleach catalysts or peracids. Preferred non-bleaching adjuncts include detersive surfactants, detergent builders, non-bleaching enzymes having a useful function in detergents, and the like. Preferred cleaning compositions herein can incorporate a source of hydrogen peroxide which is any common hydrogen-peroxide releasing salt, such as sodium perborate, sodium percarbonate, and mixtures thereof. Also useful are other sources of available oxygen such as persulfate (e.g., OXONE, manufactured by DuPont), as well as preformed organic peracids.

In a hard surface cleaning or fabric laundering operation which uses the present invention compositions, the target substrate, that is, the material to be cleaned, will typically be a fabric or surface stained with, for example, various hydrophilic food stains, such as coffee, tea or wine; with hydrophobic stains such as greasy or carotenoid stains; or is a "dingy" surface, for example one yellowed by the presence of a relatively uniformly distributed fine residue of hydrophobic soils.

In the preferred laundry compositions, adjuncts such as builders including zeolites and phosphates, surfactants such as anionic and/or nonionic and/or cationic surfactants, dispersant polymers (which modify and inhibit crystal growth of calcium and/or magnesium salts), chelants (which control wash water introduced transition metals), alkalis (to adjust pH), and detersive enzymes are present. Additional bleach-modifying adjuncts such as conventional bleach activators such as TAED and/or NOBS may be added, provided that any such materials are delivered in such a manner as to be compatible with the purposes of the present invention. The present detergent or detergent-additive compositions may, moreover, comprise one or more processing aids, fillers, perfumes, conventional enzyme particle-making materials including enzyme cores or "nonpareils", as well as pigments, and the like. In the preferred laundry compositions, additional ingredients such as soil release polymers, brighteners, and/or dye transfer inhibitors can be present.

The inventive compositions can include laundry detergents, hard-surface cleaners and the like which include all the components needed for cleaning; alternatively, the compositions can be made for use as cleaning additives. A cleaning additive, for example, can be a composition containing the transition-metal bleach catalyst, a detersive surfactant, and a builder, and can be sold for use as an "add-on", to be used with a conventional detergent which contains a perborate, percarbonate, or other primary oxidant. The compositions herein can include automatic dishwashing compositions (ADD) and denture cleaners, thus, they are not, in general, limited to fabric washing.

In general, adjunct materials used for the production of ADD compositions herein are preferably checked for compatibility with spotting/filming on glassware. Test methods for spotting/filming are generally described in the automatic dishwashing detergent literature, including DIN test methods. Certain oily materials, especially those having longer hydrocarbon chain lengths, and insoluble materials such as clays, as well as long-chain fatty acids or soaps which form soap scum are therefore preferably limited or excluded from such compositions.

Amounts of the essential ingredients can vary within wide ranges, however preferred cleaning compositions herein (which have a 1% aqueous solution pH of from about 6 to about 13, more preferably from about 7.5 to about 11.5, and most preferably less than about 11, especially from about 9 to about 10.5) are those wherein there is present: from about 0.01 ppm to about 500 ppm of a transition-metal bleach catalyst in accordance with the invention, and the balance, typically from at least about 90% to about 100% of one or more laundry or cleaning adjuncts. In preferred embodiments, there can be present (also expressed as a percentage by weight of the entire composition) from 0.1% to about 90%, preferably from about 0.5% to about 50% of a primary oxidant, such as a preformed peracid or a source of hydrogen peroxide; from 0% to about 20%, preferably at least about 0.001%, of a conventional bleach-promoting adjunct, such as a hydrophilic bleach activator, a hydrophobic bleach activator, or a mixture of hydrophilic and hydrophobic bleach activators, and at least about 0.001%, preferably from about 1% to about 40%, of a laundry or cleaning adjunct which does not have a primary role in bleaching, such as a detersive surfactant, a detergent builder, a detergent enzyme, a stabilizer, a detergent buffer, or mixtures thereof. Such fully-formulated embodiments desirably comprise, by way of non-bleaching adjuncts, from about 0.1% to about 15% of a polymeric dispersant, from about 0.01% to about 10% of a chelant, and from about 0.00001% to about 10% of a detersive enzyme though further additional or adjunct ingredients, especially colorants, perfumes, pro-perfumes (compounds which release a fragrance when triggered by any suitable trigger such as heat, enzyme action, or change in pH) may be present. Preferred adjuncts herein are selected from bleach-stable types, though bleach-unstable types can often be included through the skill of the formulator.

Detergent compositions herein can have any desired physical form; when in granular form, it is typical to limit water content, for example to less than about 10%, preferably less than about 7% free water, for best storage stability. However, liquid forms using both aqueous and/or nonaqueous solvents are also included.

Further, preferred compositions of this invention include those which are substantially free of chlorine bleach. By "substantially free" of chlorine bleach is meant that the formulator does not deliberately add a chlorine-containing bleach additive, such as hypochlorite or a source thereof, such as a chlorinated isocyanurate, to the preferred composition. However, it is recognized that because of factors outside the control of the formulator, such as chlorination of the water supply, some non-zero amount of chlorine bleach may be present in the wash liquor. The term "substantially free" can be similarly constructed with reference to preferred limitation of other ingredients, such as phosphate builder.

In a fabric laundering operation, the target substrate will typically be a fabric stained with, for example, various food stains. The test conditions will vary, depending on the type of washing appliance used and the habits of the user. Thus, front-loading laundry washing machines of the type employed in Europe generally use less water and higher detergent concentrations than do top-loading U.S.-style machines. Some machines have considerably longer wash cycles than others. Some users elect to use very hot water; others use warm or even cold water in fabric laundering operations. Of course, the catalytic performance of the transition-metal bleach catalyst will be affected by such considerations, and the levels of transition-metal bleach catalyst used in fully-formulated detergent and bleach compositions can be appropriately adjusted. As a practical matter, and not by way of limitation, the compositions and processes herein can be adjusted to provide on the order of at least one part per million of the active transition-metal bleach catalyst, in the aqueous washing liquor, and will preferably provide from about 0.01 ppm to about 1.0 ppm, more preferably from about 0.03 ppm to about 0.6 ppm, of the transition-metal bleach catalyst, in the laundry liquor. To illustrate this point further, on the order of 3 micromolar transition-metal bleach catalyst is effective at 40° C., pH 10 under European conditions using perborate and a bleach activator (e.g., nonanoyloxybenzenesulfonate). An increase in concentration of 3–5 fold may be required under U.S. conditions to achieve the same results. Conversely, use of a bleach activator and the transition-metal bleach catalyst with perborate may allow the formulator to achieve equivalent bleaching at lower perborate usage levels than products without the transition-metal bleach catalyst.

The bulk density of granular detergent compositions in accordance with the present invention typically have a bulk density of at least 600 g/liter, more preferably from 650 g/liter to 1200 g/liter. Bulk density is measured by means of a simple funnel and cup device consisting of a conical funnel molded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 ml.

To carry out a measurement, the funnel is filled with powder by hand pouring, the flap valve is opened and powder allowed to overfill the cup. The filled cup is removed from the frame and excess powder removed from the cup by passing a straight edged implement e.g.; a knife, across its upper edge. The filled cup is then weighed and the value obtained for the weight of powder doubled to provide a bulk density in g/liter. Replicate measurements are made as required.

The instant compositions may include a detersive surfactant as a preferred component. Detersive surfactants are extensively illustrated in U.S. Pat. No. 3,929,678, Dec. 30, 1975 Laughlin, et al, and U.S. Pat. No. 4,259,217, Mar. 31, 1981, Murphy; in the series "Surfactant Science", Marcel Dekker, Inc., New York and Basel; in "Handbook of Surfactants", M. R. Porter, Chapman and Hall, 2nd Ed., 1994; in "Surfactants in Consumer Products", Ed. J. Falbe, Springer-Verlag, 1987; and in numerous detergent-related patents assigned to Procter & Gamble and other detergent and consumer product manufacturers. The preferred detersive surfactant herein therefore includes anionic, nonionic, zwitterionic or amphoteric types of surfactant known for use as cleaning agents in textile laundering. Detersive surfactants useful herein are typically present at levels from 1% to 55%, by weight.

Preferred detersive surfactants are: acid, sodium and ammonium $C_9$–$C_{20}$ alkylbenzenesulfonates, particularly sodium linear secondary alkyl $C_{10}$–$C_{15}$ benzenesulfonates (1), including straight-chain and branched forms; olefinsulfonate salts, (2), that is, material made by reacting olefins, particularly $C_{10}$–$C_{20}$ α-olefins, with sulfur trioxide and then neutralizing and hydrolyzing the reaction product; sodium and ammonium $C_7$–$C_{12}$ dialkyl sulfosuccinates, (3); alkane monosulfonates, (4), such as those derived by reacting $C_8$–$C_{20}$ α-olefins with sodium bisulfite and those derived by reacting paraffins with $SO_2$ and $Cl_2$ and then hydrolyzing with a base to form a random sulfonate; α-Sulfo fatty acid salts or esters, (10); sodium alkylglycerylsulfonates, (11), especially those ethers of the higher alcohols derived from tallow or coconut oil and synthetic alcohols derived from petroleum; alkyl or alkenyl sulfates, (15), which may be primary or secondary, saturated or unsaturated, branched or unbranched. Such compounds when branched can be random or regular. When secondary, they preferably have formula $CH_3(CH_2)_x(CHOSO_3^-M^+)$ $CH_3$ or $CH_3(CH_2)_y(CHOSO_3^-M^+)$ $CH_2CH_3$ where x and (y+1) are integers of at least 7, preferably at least 9 and M is a water-soluble cation, preferably sodium. When unsaturated, sulfates such as oleyl sulfate are preferred, while the sodium and ammonium alkyl sulfates, especially those produced by sulfating $C_8$–$C_{18}$ alcohols, produced for example from tallow or coconut oil are also useful; also preferred are the alkyl or alkenyl ether sulfates, (16), especially the ethoxy sulphates having about 0.5 moles or higher of ethoxylation, preferably from 0.5–8; the alkylethercarboxylates, (19), especially the EO 1–5 ethoxycarboxylates; soaps or fatty acids (21), preferably the more water-soluble types; aminoacid-type surfactants, (23), such as sarcosinates, especially oleyl sarcosinate; phosphate esters, (26); alkyl or alkylphenol ethoxylates, propoxylates and butoxylates, (30), especially the ethoxylates "AE", including the so-called narrow peaked alkyl ethoxylates and $C_6$–$C_{12}$ alkyl phenol alkoxylates as well as the products of aliphatic primary or secondary linear or branched $C_8$–$C_{18}$ alcohols with ethylene oxide, generally 2–30 EO; N-alkyl polyhydroxy fatty acid amides especially the $C_{12}$–$C_{18}$ N-methylglucamides, (32), see WO 9206154, and N-alkoxy polyhydroxy fatty acid amides, such as $C_{10}$–$C_{18}$ N-(3-methoxypropyl) glucamide while N-propyl through N-hexyl $C_{12}$–$C_{18}$ glucamides can be used for low sudsing; alkyl polyglycosides, (33); amine oxides, (40), preferably alkyldimethylamine N- oxides and their dihydrates; sulfobetaines or "sultaines", (43); betaines (44); and gemini surfactants.

Preferred levels of anionic detersive surfactants herein are in the range from about 3% to about 30% or higher, preferably from about 8% to about 20%, more preferably still, from about 9% to about 18% by weight of the detergent composition. Preferred levels of nonionic detersive surfactant herein are from about 1% to about 20%, preferably from about 3% to about 18%, more preferably from about 5% to about 15%. Desirable weight ratios of anionic:nonionic surfactants in combination include from 1.0:9.0 to 1.0:0.25, preferably 1.0:1.5 to 1.0:0.4. Preferred levels of cationic detersive surfactant herein are from about 0.1% to about 10%, preferably from about 1% to about 3.5%, although much higher levels, e.g., up to about 20% or more, may be useful especially in nonionic :cationic (i.e., limited or anionic-free) formulations. Amphoteric or zwitterionic detersive surfactants when present are usually useful at levels in the range from about 0.1% to about 20% by weight of the detergent composition. Often levels will be limited to about 5% or less, especially when the amphoteric is costly.

The surfactant system herein is preferably present in granular compositions in the form of surfactant agglomerate particles, which may take the form of flakes, prills, marumes, noodles, ribbons, but preferably take the form of granules. The most preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands, and Gebruder Lödige Maschinenbau GmbH, D-4790 Paderborn 1, Elsenerstrasse 7–9, Postfach 2050, Germany. Most preferably a high shear mixer is used, such as a Lödige CB (Trade Name).

A high active surfactant paste comprising from 50% by weight to 95% by weight, preferably 70% by weight to 85% by weight of surfactant is typically used. The paste may be pumped into the agglomerator at a temperature high enough to maintain a pumpable viscosity, but low enough to avoid degradation of the anionic surfactants used. An operating temperature of the paste of 50° C. to 80° C. is typical.

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 40 g to 300 g of product dissolved or dispersed in a wash solution of volume from 5 to 65 liters, as are typical product dosages and wash solution volumes commonly employed in conventional machine laundry methods.

As noted, the surfactants are used herein at levels which are effective for achieving at least a directional improvement in cleaning performance. In the context of a fabric laundry composition, such "usage levels" can vary depending not only on the type and severity of the soils and stains, but also on the wash water temperature, the volume of wash water and the type of washing machine.

Any suitable methods for machine washing or cleaning soiled tableware, particularly soiled silverware are envisaged.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition in accord with the invention. By an effective amount of the machine dishwashing composition it is meant from 8 g to 60 g of product dissolved or dispersed in a wash solution of volume from 3 to 10 liters, as are typical product dosages and wash solution volumes commonly employed in conventional machine dishwashing methods.

EXAMPLE 13

Dichloro Manganese (II) 5,8 Dimethyl-1,5,8,12-tetraazabicyclo[10.3.2] heptadecane Synthesis

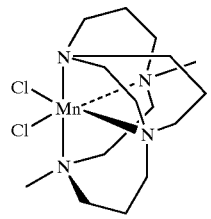

Synthesis of 1,5,9,13-Tetraazatetracyclo[11.2.2.2$^{5,9}$]heptadecane 1,4,8,12-tetraazacyclopentadecane (4.00 g, 18.7 mmol) is suspended in acetonitrile (30 mL) under nitrogen and to this is added glyoxal (3.00 g, 40% aqueous, 20.7 mmol). The resulting mixture is heated at 65° C. for 2 hours. The acetonitrile is removed under reduced pressure. Distilled water (5 mL) is added and the product is extracted with chloroform (5×40 mL). After drying over anhydrous sodium sulfate and filtration, the solvent is removed under reduced pressure. The product is then chromatographed on neutral alumina (15×2.5 cm) using chloroform/methanol (97.5:2.5 increasing to 95:5). The solvent is removed under reduced pressure and the resulting oil is dried under vacuum, overnight. Yield: 3.80 g, I (87%).

Synthesis of 1,13-Dimethyl-1,13-diazonia-5,9-diazatetracyclo[1 1.2.2.2$^{5,9}$]heptadecane diiodide 1,5,9,13-tetraazatetracyclo[11.2.2.2$^{5,9}$]heptadecane (5.50 g, 23.3 mmol) is dissolved in acetonitrile (180 mL) under nitrogen. Iodomethane (21.75 mL, 349.5 mmol) is added and the reaction is stirred at RT for 10 days. The solution is rotovapped down to a dark brown oil. The oil is taken up in absolute ethanol (100 mL) and this solution is refluxed 1 hour. During that time, a tan solid formed which is separated from the mother liquor by vacuum filtration using Whatman #1 filter paper. The solid is dried under vacuum, overnight. Yield: 1.79 g, II, (15%). Fab Mass Spec. TG/G, MeOH) M$^+$ 266 mu, 60%, MI$^+$ 393 mu, 25%.

Synthesis of 5,8 Dimethyl-1,5,8,12-tetraazabicyclo [10.3.2]heptadecane

To a stirred solution of II, (1.78 g, 3.40 mmol) in ethanol (100 mL, 95%) is added sodium borohydride (3.78 g. 0.100 mmol). The reaction is stirred under nitrogen at RT for 4 days. 10% Hydrochloric acid is slowly added until the pH is 1–2 to decompose the unreacted NaBH$_4$. Ethanol (70 mL) is then added. The solvent is removed by roto-evaporation under reduced pressure. The product is then dissolved in aqueous KOH (125 mL, 20%), resulting in a pH 14 solution. The product is then extracted with benzene (5×60 mL) and the combined organic layers are dried over anhydrous sodium sulfate. After filtering, the solvent is removed under reduced pressure. The residue is slurried with crushed KOH and then distilled at 97° C. at −1 mm pressure. Yield: 0.42 g, III, 47%. Mass Spec. (D-Cl/NH$_3$/CH$_2$Cl$_2$) MH$^+$, 269 mu, 100%.

Synthesis of Dichloro Manganese (II) 5,8 Dimethyl-1,5,8,12-tetraazabicyclo[1 0.3.2] heptadecane The ligand III, (0.200 g, 0.750 mmol) is dissolved in acetonitrile (4.0 mL) and is added to maganese(II) dipyridine dichloride (0.213 g, 0.75 mmol). The reaction is stirred for four hours at RT to yield a pale gold solution. The solvent is removed under reduced pressure. Sodium thiocyanate (0.162 g, 2.00 mmol) dissolved in methanol (4 mL) is then added. The reaction is heated 15 minutes. The reaction solution is then filtered through celite and allowed to evaporate. The resulting crystals are washed with ethanol and dried under vacuum. Yield: 0.125 g, 38%. This solid contains NaCl so it is recrystallized in acetonitrile to yield 0.11 g off a white solid. Elemental analysis theoretical: % C, 46.45, % H, 7.34, % N, 19.13. Found: % C, 45.70, % H, 7.10, % N, 19.00.

What is claimed is:

1. A metal complex comprising Mn(II), Mn(III), Mn(IV), or Mn(V); and a cross-bridged ligand having the formula:

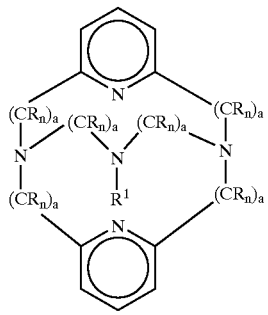

wherein in this formula:

each "n" is independently 1 or 2;

each "R" and "R$^1$" moiety is independently selected from the group consisting of H, alkyl, alkenyl, alkynyl, aryl, alkylaryl, alkylheteroaryl and heteroaryl, or at least one R moiety is covalently bonded to another R moiety and/or R$^1$ moiety to form an aromatic, heteroaromatic, cycloalkyl or heterocycloalkyl ring; said moieties, except for H, being linear or branched and substituted or unsubstituted each "a" is an integer independently selected from 1, 2 and 3.

2. A metal complex comprising Mn(II), Mn(III), Mn(IV), or Mn(V); and a cross-bridged ligand having the formula:

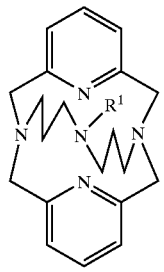

wherein "R$^1$" is independently selected from the group consisting of H, C$_1$–C$_{20}$ alkyl, alkenyl and alkynyl; said C$_1$–C$_{20}$ alkyl, alkenyl and alkynyl moieties being linear or branched and substituted or unsubstituted.

3. A metal complex comprising a transition metal atom selected from the group consisting of Mn(II), Mn(III), Mn(IV), Mn(V), Fe(II), Fe(III), Fe(IV), Cr(II), Cr(III), Cr(IV), Cr(V), and Cr(VI); and a cross-bridged macropolycyclic ligand having the formula:

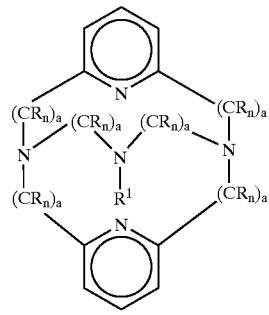

wherein:

each "n" is independently 1 or 2;

each "R" and "R$^1$" moiety is independently selected from the group consisting of H, alkyl, alkenyl, alkynyl, aryl, alkylaryl, alkylheteroaryl, and heteroaryl, or at least one R moiety is covalently bonded to another R moiety and/or R$^1$ moiety to form an aromatic, heteroaromatic, cycloalkyl or heterocycloalkyl ring, said moieties, except for H, being linear or branched and substituted or unsubstituted;

each "a" is independently 2 or 3; and all nitrogen atoms in the macropolycyclic rings are coordinated to the transition metal atom.

4. A metal complex comprising a transition metal atom selected from the group consisting of Mn(II), Mn(III), Mn(IV), Mn(V), Fe(II), Fe(III), Fe(IV), Cr(II), Cr(III), Cr(IV), Cr(V), and Cr(VI); and a cross-bridged macropolycyclic ligand having the formula:

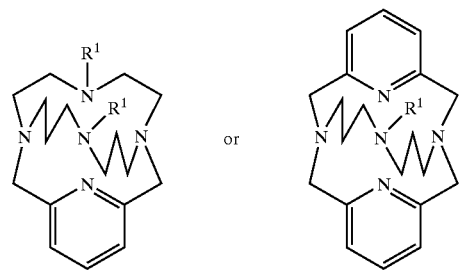

wherein "R$^1$" is independently selected from the group consisting of H, C$_1$–C$_{20}$ alkyl, alkenyl and alkynyl; said C$_1$–C$_{20}$ alkyl, alkenyl and alkynyl moieties being linear or branched and substituted or unsubstituted; and all nitrogen atoms in the macropolycyclic rings are coordinated to the transition metal atom.

* * * * *